US008790698B2

(12) United States Patent
Odar et al.

(10) Patent No.: US 8,790,698 B2
(45) Date of Patent: *Jul. 29, 2014

(54) USE OF A REGENERATIVE BIOFUNCTIONAL COLLAGEN BIOMATRIX FOR TREATING VISCERAL OR PARIETAL DEFECTS

(75) Inventors: Johann Odar, Muehlhausen (DE); Raymond Nistor-Gallo, Baden (AT); Laura Caliari, Rome (IT)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 893 days.

This patent is subject to a terminal disclaimer.

(21) Appl. No.: 12/260,394

(22) Filed: Oct. 29, 2008

(65) Prior Publication Data

US 2009/0142396 A1     Jun. 4, 2009

Related U.S. Application Data

(60) Provisional application No. 60/983,776, filed on Oct. 30, 2007.

(51) Int. Cl.
| | |
|---|---|
| A61K 9/14 | (2006.01) |
| A61K 38/31 | (2006.01) |
| A61K 47/48 | (2006.01) |
| A61L 31/14 | (2006.01) |
| A61L 31/04 | (2006.01) |

(52) U.S. Cl.
CPC ............... *A61L 31/044* (2013.01); *A61L 31/14* (2013.01)
USPC ......................................... 424/484; 514/17.2

(58) Field of Classification Search
USPC .......................................... 424/484; 514/17.2
See application file for complete search history.

(56) References Cited

U.S. PATENT DOCUMENTS

| | | | |
|---|---|---|---|
| 2,507,244 A | 5/1950 | Correll | |
| 2,558,395 A | 6/1951 | Studer | |
| 4,013,078 A | 3/1977 | Field | |
| 4,124,705 A | 11/1978 | Rothman et al. | |
| 4,164,559 A | 8/1979 | Miyata et al. | |
| 4,179,400 A | 12/1979 | Tsao et al. | |
| 4,265,233 A | 5/1981 | Sugitachi et al. | |
| 4,291,013 A | 9/1981 | Wahlig et al. | |
| 4,292,972 A | 10/1981 | Pawelchak et al. | |
| 4,298,598 A | 11/1981 | Schwarz et al. | |
| 4,300,494 A | 11/1981 | Graiff et al. | |
| 4,347,234 A | 8/1982 | Wahlig et al. | |
| 4,362,567 A | 12/1982 | Schwarz et al. | |
| 4,377,572 A | 3/1983 | Schwarz et al. | |
| 4,424,208 A | 1/1984 | Wallace et al. | |
| 4,453,939 A | 6/1984 | Zimmerman et al. | |
| 4,482,386 A | 11/1984 | Wittwer et al. | |
| 4,515,637 A | 5/1985 | Cioca | |
| 4,536,387 A | 8/1985 | Sakamoto et al. | |
| 4,540,410 A | 9/1985 | Wood et al. | |
| 4,543,332 A | 9/1985 | Jao et al. | |
| 4,554,156 A | 11/1985 | Fischer | |
| 4,600,574 A | 7/1986 | Lindner et al. | |
| 4,640,834 A | 2/1987 | Eibl et al. | |
| 4,655,211 A | 4/1987 | Sakamoto et al. | |
| 4,746,514 A | 5/1988 | Warne | |
| 4,749,689 A | 6/1988 | Miyata et al. | |
| 4,803,075 A | 2/1989 | Wallace et al. | |
| 4,818,517 A | 4/1989 | Kwee et al. | |
| 4,832,686 A | 5/1989 | Anderson | |
| 4,837,285 A | 6/1989 | Berg et al. | |
| 4,891,359 A | 1/1990 | Saferstein et al. | |
| 4,925,677 A | 5/1990 | Feijen | |
| 4,946,870 A | 8/1990 | Partain, III. et al. | |
| 5,007,916 A | 4/1991 | Linsky et al. | |
| 5,017,229 A | 5/1991 | Burns et al. | |
| 5,023,082 A | 6/1991 | Friedman et al. | |
| 5,041,292 A | 8/1991 | Feijen | |
| 5,061,274 A | 10/1991 | Kensey | |
| 5,061,492 A | 10/1991 | Okada et al. | |
| 5,080,893 A | 1/1992 | Goldberg et al. | |
| 5,108,421 A | 4/1992 | Fowler | |
| 5,126,141 A | 6/1992 | Henry | |

(Continued)

FOREIGN PATENT DOCUMENTS

| | | |
|---|---|---|
| CA | 2173508 A1 | 10/1996 |
| EP | 0132983 A | 2/1985 |

(Continued)

OTHER PUBLICATIONS

The Free Dictionary, obtained online at: http://www.thefreedictionary.com/p/couple, downloaded on Jan. 5, 2012.*

(Continued)

*Primary Examiner* — Abigail Fisher
(74) *Attorney, Agent, or Firm* — Kilpatrick Townsend Stockton LLP

(57) ABSTRACT

Techniques for treating visceral or parietal membrane and tissue defects include the application of a collagen biomatrix to the defect to repair and regenerate a visceral or parietal membrane, for example in patients suffering tissue defects or undergoing visceral or parietal surgical treatment. Such approaches avoid persistent tissue leaks and their consequences such as fluid leaks and air leaks. The use of collagen biomatrix, optionally in conjunction with a fibrin sealant, an anti-adhesive, or both, can minimize tissue leaks or fluid leaks in injured patients suffering tissue defects or subjects undergoing surgery such as visceral or parietal resections and other operations.

23 Claims, 28 Drawing Sheets

(56) References Cited

U.S. PATENT DOCUMENTS

| | | |
|---|---|---|
| 5,129,882 A | 7/1992 | Weldon et al. |
| 5,134,229 A | 7/1992 | Saferstein et al. |
| 5,135,751 A | 8/1992 | Henry et al. |
| 5,135,755 A | 8/1992 | Czech et al. |
| 5,140,016 A | 8/1992 | Goldberg et al. |
| 5,149,540 A | 9/1992 | Kunihiro |
| 5,162,430 A | 11/1992 | Rhee et al. |
| 5,165,938 A | 11/1992 | Knighton |
| 5,178,883 A | 1/1993 | Knighton |
| 5,192,300 A | 3/1993 | Fowler |
| 5,196,185 A | 3/1993 | Silver et al. |
| 5,204,382 A | 4/1993 | Wallace et al. |
| 5,209,776 A | 5/1993 | Bass et al. |
| 5,219,328 A | 6/1993 | Morse et al. |
| 5,275,616 A | 1/1994 | Fowler |
| 5,292,362 A | 3/1994 | Bass et al. |
| 5,300,494 A | 4/1994 | Brode, II et al. |
| 5,304,377 A | 4/1994 | Yamada et al. |
| 5,306,501 A | 4/1994 | Viegas et al. |
| 5,324,775 A | 6/1994 | Rhee et al. |
| 5,328,955 A | 7/1994 | Rhee et al. |
| 5,330,446 A | 7/1994 | Weldon et al. |
| 5,350,573 A | 9/1994 | Goldberg et al. |
| 5,352,715 A | 10/1994 | Wallace et al. |
| 5,356,614 A | 10/1994 | Sharma |
| 5,384,333 A | 1/1995 | Davis et al. |
| 5,385,606 A | 1/1995 | Kowanko |
| 5,399,361 A | 3/1995 | Song et al. |
| 5,418,222 A | 5/1995 | Song et al. |
| 5,428,022 A | 6/1995 | Palefsky et al. |
| 5,428,024 A | 6/1995 | Chu et al. |
| 5,437,672 A | 8/1995 | Alleyne |
| 5,447,966 A | 9/1995 | Hermes et al. |
| 5,478,352 A | 12/1995 | Fowler |
| 5,507,744 A | 4/1996 | Tay et al. |
| 5,510,418 A | 4/1996 | Rhee et al. |
| 5,512,301 A | 4/1996 | Song et al. |
| 5,514,379 A | 5/1996 | Weissleder et al. |
| 5,516,532 A | 5/1996 | Atala et al. |
| 5,520,925 A | 5/1996 | Maser |
| 5,531,759 A | 7/1996 | Kensey et al. |
| 5,540,715 A | 7/1996 | Katsaros et al. |
| 5,580,923 A * | 12/1996 | Yeung et al. ............ 525/54.1 |
| 5,595,735 A | 1/1997 | Saferstein et al. |
| 5,614,587 A | 3/1997 | Rhee et al. |
| 5,618,551 A | 4/1997 | Tardy et al. |
| 5,648,506 A | 7/1997 | Desai et al. |
| 5,662,598 A * | 9/1997 | Tobin ........................ 602/41 |
| 5,667,839 A | 9/1997 | Berg |
| 5,672,336 A | 9/1997 | Sharma |
| 5,674,275 A | 10/1997 | Tang et al. |
| 5,690,675 A | 11/1997 | Sawyer et al. |
| 5,698,213 A | 12/1997 | Jamiolkowski et al. |
| 5,714,370 A | 2/1998 | Eibl et al. |
| 5,853,749 A | 12/1998 | Hobbs |
| 5,874,500 A | 2/1999 | Rhee et al. |
| 5,902,832 A | 5/1999 | Van Bladel et al. |
| 5,908,054 A | 6/1999 | Safabash et al. |
| 5,931,165 A | 8/1999 | Reich et al. |
| 5,997,895 A | 12/1999 | Narotam et al. |
| 6,063,061 A | 5/2000 | Wallace et al. |
| 6,066,325 A | 5/2000 | Wallace et al. |
| 6,110,484 A | 8/2000 | Sierra |
| 6,129,761 A | 10/2000 | Hubbell |
| 6,166,130 A | 12/2000 | Rhee et al. |
| 6,179,872 B1 | 1/2001 | Bell et al. |
| 6,277,394 B1 | 8/2001 | Sierra |
| 6,312,474 B1 | 11/2001 | Francis et al. |
| 6,312,725 B1 | 11/2001 | Wallace et al. |
| 6,328,229 B1 | 12/2001 | Duronio et al. |
| 6,440,167 B2 | 8/2002 | Shimizu |
| 6,458,386 B1 | 10/2002 | Schacht et al. |
| 6,458,889 B1 | 10/2002 | Trollsas |
| 6,624,245 B2 | 9/2003 | Wallace et al. |
| 6,706,690 B2 | 3/2004 | Reich et al. |
| 7,320,962 B2 | 1/2008 | Reich et al. |
| 7,435,425 B2 | 10/2008 | Qian et al. |
| 7,547,446 B2 | 6/2009 | Qian et al. |
| 7,871,637 B2 | 1/2011 | Qian et al. |
| 2001/0016205 A1 | 8/2001 | Shimizu |
| 2002/0193448 A1 | 12/2002 | Wallace et al. |
| 2003/0064109 A1 | 4/2003 | Qian et al. |
| 2005/0142162 A1* | 6/2005 | Hunter et al. ............ 424/423 |
| 2006/0147492 A1 | 7/2006 | Hunter et al. |
| 2006/0167561 A1 | 7/2006 | Odar et al. |
| 2006/0246105 A1* | 11/2006 | Molz et al. ............... 424/423 |
| 2008/0085316 A1 | 4/2008 | Qian et al. |
| 2008/0091277 A1 | 4/2008 | Deusch et al. |
| 2008/0286376 A1 | 11/2008 | Qian et al. |
| 2010/0028309 A1 | 2/2010 | Odar et al. |
| 2010/0292717 A1 | 11/2010 | Petter-Puchner et al. |
| 2010/0318048 A1 | 12/2010 | Hoefinghoff et al. |

FOREIGN PATENT DOCUMENTS

| | | |
|---|---|---|
| EP | 0376931 | 7/1990 |
| EP | 0132983 B2 | 12/1991 |
| EP | 0493387 | 7/1992 |
| EP | 781564 A2 * | 7/1997 |
| EP | 0891193 | 1/1999 |
| EP | 0612252 B1 | 5/1999 |
| EP | 1084720 A1 | 3/2001 |
| EP | 1283063 A1 | 2/2003 |
| EP | 1484070 A1 | 12/2004 |
| EP | 01414370 B1 | 4/2007 |
| JP | 59-113889 | 6/1984 |
| JP | 05308969 | 11/1993 |
| JP | 6-254148 | 9/1994 |
| JP | 08-266613 A | 10/1996 |
| JP | 9-504719 | 5/1997 |
| JP | 07090241 | 4/2007 |
| KR | 10-1991-0007847 B1 | 10/1991 |
| WO | WO 86/00912 | 2/1986 |
| WO | WO 92/21354 | 12/1992 |
| WO | WO 94/27630 A1 | 12/1994 |
| WO | WO 95/12371 | 5/1995 |
| WO | WO 92/22252 | 6/1995 |
| WO | WO 95/15747 | 6/1995 |
| WO | WO 96/04025 | 2/1996 |
| WO | WO 96/06883 | 3/1996 |
| WO | WO 96/10374 | 4/1996 |
| WO | WO 96/10428 | 4/1996 |
| WO | WO 96/14368 | 5/1996 |
| WO | WO 96/39159 | 12/1996 |
| WO | WO 97/37694 A1 | 10/1997 |
| WO | WO 98/08550 A1 | 3/1998 |
| WO | WO 99/13902 A1 | 3/1999 |
| WO | WO 02/22184 A2 | 3/2002 |
| WO | WO 02-070594 A2 | 9/2002 |
| WO | WO 03/0007845 A1 | 1/2003 |
| WO | WO 2004/108179 A1 | 12/2004 |
| WO | WO 2005/094915 A1 | 10/2005 |
| WO | WO 2006/031358 A | 3/2006 |
| WO | WO 2006/118460 A1 | 11/2006 |
| WO | WO 2007/001926 A2 | 1/2007 |
| WO | WO 2007/137839 A2 | 12/2007 |
| WO | WO 2007/137839 A3 | 12/2007 |
| WO | WO 2008/016983 A2 | 2/2008 |

OTHER PUBLICATIONS

Barrow, D.L., et al.; "The Use of Greater Omentum Vascularized Free Flaps for Neurosurgical Disorders Requiring Reconstruction"; J. Neurosurg.; vol. 60; pp. 305-311 (Feb. 1984).

Baxter product brochure for TissuFleece E, TissuCone E and TissuFoil E (2003).

Baxter Product Catalogue; Collagen; 4 pages (2006).

Chaplin, J.M., et al.; "Use of an Acellular Dermal Allograft for Dural Replacement: An Experimental Study"; Neurosurgery: vol. 45:2; pp. 320-327 (Aug. 1999).

Collins, Ronald et al., "Use of Collagen Film as a Dural Substitute: Preliminary Animal Studies", Journal of Biomedical Materials Research, vol. 25, 267-276 (1991).

(56) References Cited

OTHER PUBLICATIONS

Filippi, R., et al.; "Bovine Pericardium for Duraplasty: Clinical Results in 32 Patients"; Neurosurg. Rev.; vol. 20; pp. 103-107 (2001).
Hieb, Lee D. et al., "Spontaneous Postoperative Cerebrospinal Fluid Leaks Following Application of Anti-Adhesion Barrier Gel", Spine vol. 26, No. 7, pp. 748-751, 2001.
Kim, Kee D., et al., "Reduction in Leg Pain and Lower-Extremity Weakness with Oxiplex/SP Gel for 1 Year after Laminactomy, Laminotomy, and Disectomy", Neurosurg Focus 17 (1): Clinical Pearl 1, Jul. 2004, pp. 1-6.
Kline, D.G.; "Dural Replacement with Resorbable Collagen"; Arch Surg; vol. 91; pp. 924-929 (Dec. 1965).
Kuhn, J. et al., "Bilateral Subdural Haemotomata and Lumbar Pseudomeningocele Due to a Chronic Leakage of Liquor Cerebrospinalis after a Lumbar Disectomy with the Application of ADCON-L Gel", J. Neural Neurosurg. Psychiarty 2005; 76: 1031-1033.
Laquerriere, A., et al.; "Experimental Evaluation of Bilayered Human Collagen as a Dural Substitute"; J. Neurosurg; vol. 78; pp. 487-491 (Mar. 1993).
Le, Anh X. et al., "Unrecognized Durotomy After Lumbar Discectomy: A Report of Four Cases Associated with the Use of ADCON-L", Spine vol. 26, No. 1, pp. 115-118, 2001.
Lee, J.F., et al.; "Experimental Evaluation of Silicone-Coated Dacron and Collagen Fabric-Film Laminate as Dural Substitutes"; J. Neurosurg.; vol. 27; pp. 558-564 (Apr. 1967).
Matsumoto, K., et al.; "A Gelatin Coated Collagen-Polyglycolic Acid Composite Membrane as a Dural Substitute"; ASAIO Journal; pp. 641-645 (2001).
Maurer, P.K., et al.; "Vicryl (Polyglactin 910) Mesh as a Dural Substitute"; J Neurosurg; vol. 63; pp. 448-452 (Sep. 1985).
Meddings, N., et al.; "Collagen Vicryl—A New Dural Prosthesis"; Acta Neurochir; vol. 117; pp. 53-58 (1992).
Mello, L.R., et al.; "Duraplasty with Biosynthetic Cellulose: An Experimental Study"; J Neurosurg; vol. 86; pp. 143-150 (Jan. 1997).
Narotam, P.K., et al.; "A Clinicopathological Study of Collagen Sponge as a Dural Graft in Neurosurgery"; J Neurosurg; vol. 82; pp. 406-412 (Mar. 1995).
Narotam, P.K., et al.; "Experimental Evaluation of Collagen Sponge as a Dural Graft"; British Journal of Neurosurgery; vol. 7; pp. 635-641 (1993).
O'Neill, P., et al.; "Use of Porcine Dermis as Dural Substitute in 72 Patients"; J. Neurosurg.; vol. 61; pp. 351-354 (Aug. 1984).
Palm, S.J., et al.; "Dural Closure with Nonpenetrating Clips Prevents Meningoneural Adhesions: An Experimental Study in Dogs"; Neurosurgery; vol. 45:4; pp. 875-882 (Oct. 1999).
Parizek, J., et al.; "Detailed Evaluation of 2959 Allogeneic and Xenogeneic Dense Connective Tissue Grafts (Fascia Lata, Pericardium, and Dura Mater) Used in the Course of 20 Years for Duraplasty in Neurosurgery"; Acta Neurochir; vol. 139; pp. 827-838 (1997).
Park, Y-K., at al.; "Prevention of Arachnoiditis and Postoperative Tethering of the Spinal Cord with Gore-Tex Surgical Membrane: An Experimental Study with Rats"; Neurosurgery; vol. 42 :4; pp. 813-824 (Apr. 1998).
Pietrucha, K.; "New Collagen Implant as Dural Substitute"; Biomatarials; vol. 12; pp. 320-323 (Apr. 1991).
Porchet, Francois, "Inhibition of Epidural Fibrosis with ADCON-L: Effect on Clinical Outcome One Year Following Re-operation for Recurrent Lumbar Radiculopathy", 1998, pp. 1-10.
Raul, J.S., et al.; "Utilisation du Polyester Urethane (Neuro-Patch®) Comme Substitut Dural"; Neurochirugie; vol. 49:2-3; pp. 83-89 (2003).
Reddy, M., et al.; "A Clinical Study of a Fibrinogen-Based Collagen Fleece for Dural Repair in Neurosurgery"; Acta Neurochir; vol. 144; pp. 265-269 (2002).
Ross, Jeffrey S. et al., "Association Between Peridural Scar and Recurrent Radicular Pain After Lumbar Discectomy: Magnetic Resonance Evaluation", Neurosurgery, pp. 855-863, 1996.
San-Galli, F., et al.; "Experimental Evaluation of a Collagen-Coated Vicryl Mesh as a Dural Substitute"; Neurosurgery: vol. 30:3; pp. 396-401 (1992).
Shaffrey, C.I., et al.; "Neurosurgical Applications of Fibrin Glue: Augmentation of Dural Closure in 134 Patients"; Neurosurgery; vol. 26:2; pp. 207-210 (1990).
Smith, KA, et al.; "Delayed Postoperative Tethering of the Cervical Spinal Corei"; J Neurosurg; vol. 81; pp. 196-201 (Aug. 1994).
Springorum, H.W.; "Die Verwendung von Kollagenfolien zur Uberbruckung von Defekten des Gleitgewebes bei Achillotenotomien und Achillessehnenrupturen"; Akt. Traumatal.; vol. 15; pp. 120-121 (1985).
Stricker, A., et al.; "Die Verwendung von TissuFoil Membran bei der Sinusbodenaugmentation"; Ellipse; vol. 17:1; pp. 1-5 (2001).
Vinas, F.E., et al.; "Evaluation of Expanded Polytetrafluoroethylene (ePTFE) versus Polydioxanone (PDS) for the Repair of Dura Mater Defects"; Neurological Research; vol. 21; pp. 262-268 (Apr. 1999).
Warren, W.L., et al.; "Dural Repair Using Acellular Human Dermis: Experience with 200 Cases: Technique Assessment; Neurosurgery; vol. 46:6; pp. 1391-1396 (Jun. 2000).
Ziegelaar, B.W.; "Tissue Engineering of a Tracheal Equivalent", Doctoral Thesis at Ludwig Maximilians University, Munich, Germany; 25 pages (2004).
T. Kofidis et al., "Clinically established Hemostatis Scaffold (Tissue Fleece) as Biomatrix in Tissue- and organ-engineering research", Tissue Eng vol. 9, No. 3, 2003, S.517-523; ISSN: 1076-3279.
Knopp U., "A new collagen foil versus a cadaveric dura graft for dural defects—a comparative animal experimental study", EANS—12th European Congress of Neurosurgery, Lisbon, Sep. 7-12, 2003, 663-666.
Ziegelaar, BW et al., "The characterisation of human respiratory epithelial cells cultured on reabsorbable scaffolds: first steps towards a tissue engineered tracheal replacement", Biomaterials 23 (2002), 1425-1438; ISSN 0142-9612.
GentaFleece Kollagenvlies Version 5 found on internet at: http://www.advancingbiosurgery.com/en_EU/downloads/ifu_gentafleece.pdf, Mar. 2002, 2 pages.
Tissudura Kollagene Biomatrix zur Duraregeneration found on internet at: http://www.biosurgery.de/Produkte/pdf/TissueDura_GI.pdf, Aug. 2004, 4 pages.
GentaFleece Kollagenvlies Version 5 found on internet on Jan. 11, 2010 at: http://www.baxterbiosurgery.com/en_EU/downloads/ifu_gentafleece.pdf, Apr. 16, 2002, 6 pages, English portion of instructions for use.
Raul, J.S., et al.; "Utilisation du Polyester Urethane (Neuro-Patch®) Comme Substitut Dural"; Neurochirugie; vol. 49:2-3; pp. 83-89 (2003), English abstract only on p. 83.
Springorum, H.W.; "Die Verwendung von Kollagenfolien zur Uberbruckung von Defekten des Gleitgewebes bei Achillotenotomien and Achillessehnenrupturen"; Akt. Traumatal.; vol. 15; pp. 120-121 (1985), English abstract only on p. 120.
Stricker, A., et al.; "Die Verwendung von TissuFoil Membran bei der Sinusbodenaugmentation"; Ellipse; vol. 17:1; pp. 1-5 (2001), English abstract only on p. 1.
TissuFleece E, Version 5, found on internet on Jan. 11, 2010 at: http://tissuesealing.com/en_EU/downloads/ifu_tissufleece.pdf, Nov. 25, 2003, 6 pages, English portion of instructions for use.
Cheung, David T., et al., "Mechanism of crosslinking of proteins by glutaraldehyde IV: In Vitro and In Vivo stability of a crosslinked collagen matrix", Connective Tissue Research, 1990;25(1), pp. 27-34.
Jonas, Richard A., et al., "A new sealant for knitted Dacron prostheses: Minimally cross-linked gelatin", J. Vasc. Surg., Mar. 1988;7(3), pp. 414-419.
Larson, Paul O., "Topical Hemostatic Agents for Dermatologic Surgery", J. Dermatol. Surg. Oncol., Jun. 1988;14(6), pp. 623-632.
McPherson, J. M. et al., "An examination of the biologic response to injectable, glutaraldehyde cross-linked collagen implants", J. Biomed. Mater. Res., Jan. 1986;20(1), pp. 93-107.
McPherson, J. M., et al., "The preparation and physiochemical characterization of an injectable form of reconstituted, glutaraldehyde cross-linked, bovine corium collagen", J. Biomed. Mater. Res., Jan. 1986;20(1), pp. 79-92.

(56) References Cited

OTHER PUBLICATIONS

McPherson, John M., et al., "The Effects of Heparin on the Physiochemical Properties of Reconstituted Collagen", Coll. Relat. Res., Jan. 1988;8(1), pp. 65-82.
Nimni, M. E., et al., "Chemically modified collagen: A natural biomaterial for tissue replacement", J. Biomed. Mater. Res., Jun. 1987;21(6), pp. 741-771.
Nimni, Marcel E., "The cross-linking and structure modification of the collagen matrix in the design of cardiovascular prosthesis", J. of Cardiac Surgery, Dec. 1988;3(4), pp. 523-533.
Rosenblatt, Joel, et al., "Effect of electrostatic forces on the dynamic rheological properties of injectable collagen biomaterials", Biomaterials, 1992;13(12), pp. 878-886.
Rosenblatt, Joel, et al., "Injectable collagen as a pH-sensitive hydrogel", Biomaterials, Oct. 1994;15(12), pp. 985-995.
Rossler, B., et al., "Collagen microparticles: preparation and properties", J. Microencapsulation, Jan.-Feb. 1995;12(1), pp. 49-57.
Wallace, Donald G., et al., "Injectable cross-linked collagen with improved flow properties", J. of Biomedical Materials Research, Aug. 1989;23(8), pp. 931-945.
Wallace, Donald, "The relative contribution of electrostatic interactions to stabilization of collagen fibrils", Biopolymers, May-Jun. 1990; 29(6-7), pp. 1015-1026.
Ansell et al., "Gelfoam and Autologous Clot Embolization: Effect on Coagulation", *Invest. Radiol.* (1978) 13:115-120.
Boyers et al., "Reduction of Postoperative Pelvic Adhesions in the Rabbit with Gore-Tex Surguical Membrane" *Fert. Ster.* (1988) 49(6):1066-1070.
Bruck, S. D., Ed., Controlled Drug Delivery, CRC Press, Boca Raton, FL (1983) A title page and table of contents.
Cantor et al., "Gelfoam and Thrombin in Gastrointestinal Bleeding: An Experimental Study", pp. 890-893, 1950.
Cantor et al., "Gelfoam and Thrombin in Treatment of Massive Gastroduodenal Hemmorhage: A Preliminary Report" *Am J. Surg.* (1950) pp. 883-887.
Cantor et al., "Gelfoam and Thrombin in Treatment of Massive Upper Gastroduodenal Hemorrhage", *Am. J. Surg.* (1951) pp. 230-235.
Chuang et al., "Sheath Needle for Liver Biopsy in High-Risk Patients", *Radiology* (1988) 166:261-262.
Collins et al., "Enemata of Gelfoam-Milk Suspension Combined with Thrombin Solution to Control Massive Hemorrhage Following Anorectal Surgery", *Am. J. Proctol.* (1951) 2:60-63.
Edgerton et al., "Vascular Hamartomas and Hemangiomos: Classification and Treatment" *Southern Med. J.* (1982) 75(12):1541-1547.
Heller et al., "Release of Norethindrone from Poly(Ortho Esters)" *Polymer Engineering Sci.* (1981) 21:727-731.
Hood et al., "Efficacy of Topical Hemostat Floseal Matrix in Vascular Surgery," 24th World Congress of the International Society for Cardiovascular Surgery (Sep. 12-16, 1999), 2 pages total.
Hotz et al., "Collagen and Fibrin as Biologic Binders from Granular Hydroxyapatite" (abstract posted at http://www.ncbi.nlm.nih.gov/ on Jan. 3, 2001 from) *Dtsh. Z. Mund. Kiefer Geichtshir.* (1989) 13(4):296-300.

Jeong et al., "Biodegradable Block Copolymers as Injectible Drig-Delivery Systems" *Nature* (1997) 388:860-862.
Krill et al., "Topical Thrombin and Powdered Gelfoam: An Efficiaent Hemostatic Treatment for Surgery", *J. Tenn. Dent. Assoc.* (1986) 66(2):26-27.
Langer et al., "Chemical and Physical Structure of Polymerns as Carriers for Controlled Release of Bioactive Agents: A Review" *Rev. Marco Chem. Phys.* (1983) C23(1):61-126.
Leong et al., "Polyanhydrides for Controlled Release of Bioactive Agents" *Biomaterials* (1986) 7:364-371.
Leong et al., "Polymeric Controlled Drug Delivery" *Adv. Drug Delivery Rev.* (1987)1:199-233.
Maok, "Hemostatic Agents" (1991) *Today's O.R. Nurse*, pp. 6-10.
Masar et al., "Synthesis of Polyurethanes and Investigation of their Hydrolytic Stability" *J. Polymer. Sci.*, Polymer Symposium (1979) 66:259-268.
McClure et al., "Massive Gastroduodenal Hemorrhage: Treatment with Powdered Gelfoam and Buffered Thrombin Solution" *Surg.* (1952) 32:630-637.
PCT International Preliminary Report on Patentability and Written Opinion mailed Feb. 17, 2009, International Application No. PCT/US2007/074984, 8 pages.
Pitt et al., "Controlled Release of Bioactive Materials", R. Baker, Ed., Academic Press, New York, 1980.
Riley et al., "Percutaneous Liver Biopsy with Plugging of Needle Track: A Safe Method for Use in Patients with Impaired Coagulation" *Lancet* (Aug. 25, 1984) pp. 436.
Sidman et al., "Biodegradable, Implantable Sustained Release Systems Based on Glutamic Acid Copolymers" *J. Membrane Science* (1979) 7:227-291.
Sugitachi et al., "A Newly Devised Chemo-embolic Agent, G.T. XIII-ADM." (English abstract posted at http://www.ncbi.nlm.nih.gov/ on Jan. 3, 2001 from) *Gan. To. Kagaku Ryoho.* (1985) 12(10) 1942-1943.
Sugitachi et al., "Locoregional Therapy in Patients with Maignant Pleural Effusion—Two Different Kinds of BAC Therapy" (English abstract posted at http://www.ncbi.nlm.nih.gov/ on Jan. 3, 2001 from) *Gan. To. Kagaku Ryoho.* (1992) 19(10):1640-1643.
Sugitachi et al., "Preoperative Transcatheter Arterial Chemoembolization for Locally Advanced Breast Cancer: Application for New Thrombotic Materials" *Japan J. Surg.* (1983) 13(5):456-458.
Tobin et al., "Plugged Liver Biopsy in Patients with Impaired Coagulation" *Digestive Diseases and Science* (1989) 34(1):13-15.
Tucker et al., "Absorbable Gelatin (Gelfoam) Sponge" Charles T. Thomas, Publisher, Springfiled, Illinois, 3-125, 1965.
Vander Salm et al., "Reduction of Sternal Infection by Application of Topical Vancomycin" *J. Thorac. Surg.* (1989) 98:618-622.
Yuki et al., "Effects of EndoscopicVariceal Sclerotherapy using GT XIII on Blood Coagulation Tests and the Renal Kallikrein-kinin System" (English abstract posted at http://www.ncbi.nlm.nih.gov/ on Jan. 3, 2001 from) *Gastroentral. Japan* (1990) 25(5):561-567.
Zins et al., "US-Guided Percutaneous Liver Biopsy with Plugging of the Needle Track: A Prospective Study in 72 High-Rish Patients" *Radiology* (1992) 184(3):841-843.

\* cited by examiner

USE OF A REGENERATIVE BIOFUNCTIONAL COLLAGEN BIOMATRIX FOR TREATING VISCERAL OR PARIETAL DEFECTS

CROSS REFERENCES TO RELATED APPLICATIONS

This application is a nonprovisional of, and claims the benefit of priority to, U.S. Provisional Patent Application No. 60/983,776 filed Oct. 30, 2007, which is incorporated herein by reference for all purposes.

BACKGROUND OF THE INVENTION

Embodiments of the present invention encompass the use of a biofunctional, regenerative, reconstituted collagen biomatrix in conjunction with or without fibrin sealant, polyethylene glycol, or other materials, for treating defects in a visceral or parietal membrane, such as for preventing post-surgical tissue leaks and air leaks.

Prolonged postoperative tissue leaks and air leaks are a major cause of morbidity after pulmonary resection and other types of visceral or parietal membrane surgery and lead to prolonged drainage time which is associated with pain and immobilization. These complications put the patients at an increased risk for development of infections, bleeding, adhesions, pneumothorax and bronchopleural fistulae and consequently, a prolonged hospital stay, which increases healthcare costs. Surgical techniques to address this issue include the use of sutures or stapling devices with or without the concomitant use of surgical sealants, which have proven insufficient and have failed to eliminate tissue leaks or air leakage during pulmonary surgery.

A variety of complementary natural and synthetic materials have been tried with mixed results to overcome tissue leaks or air leaks during pulmonary resection. These materials include fibrin sealants and synthetic glues. In some cases, sealants have been used to enforce sutures or staple lines. However, they have had limited success and cannot replace an exact and precise surgical technique. Moreover, internal scarring, fibrosis, and adhesions after visceral or parietal membrane surgery are well known and undesired side effects of such surgery.

Consequently, a strong need exists for improved systems and techniques for directed and controlled tissue regeneration to treat or prevent post-surgical or post-traumatic tissue leaks, fluid leaks (e.g. blood, serous fluids, bile), or air leaks in lung tissue, and to promote tissue healing and regeneration process following surgical and traumatic injuries. There is also a need for matrices which do not absorb blood, which support the remodelling, regeneration, and the wound healing process, which direct the growth and the in-growth of cells. Further, there is a need for techniques that involve the replacement and regeneration of severed visceralis, such as pleura that covers the lung.

Embodiments of the present invention provide solutions for such needs. Aspects of the present invention encompass the use of a biofunctional collagen biomatrix, optionally with a fibrin sealant, for surgically treating visceral or parietal membranes and tissue defects after resection and for treating pulmonary tissue defects or defects of a visceral membrane, such as the pleura visceralis after lung resection surgery. The effectiveness of such techniques can be demonstrated by the results of an animal trial using a collagen biomatrix for the repair and regeneration of visceral defects. This collagen biomatrix provides a matrix with a special layer structure and includes pure naturally cross-linked collagen of equine origin. The biomatrix can act as a substitute for the severed visceralis or visceral membrane, and later, during the healing process as a regenerative biomatrix for the ingrowth of cells and formation of for example a visceral neo-pleura. The biomatrix may also act as an effective seal against fluid leaks, which is particularly advantageous as lung or organ function is greatly improved in the absence of fluid leaks in the visceral membrane. Relatedly, embodiments encompass the use of a collagen biomatrix for preventing post-surgical fluid leaks in pulmonary resection or other lung surgery or for treating defects of a visceral membrane such as a pleural membrane.

BRIEF SUMMARY OF THE INVENTION

Embodiments of the present invention include a novel biofunctional collagen biomatrix optionally in conjunction with fibrin sealant and its use for visceral or parietal membrane reparation, such as for pleural reparation and tissue regeneration in patients undergoing lung surgery, while avoiding or inhibiting persistent tissue leaks, air leaks, fluid leaks, and the like. The use of surgical sealants alone or as a support for staples or suture lines has not been generally effective in reducing the incidence of AALs (Alveolar Air Leaks) and PAALs (Persistent Alveolar Air Leaks). In contrast, embodiments of the present invention encompass the use of collagen foils applied optionally together with fibrin sealant on tissue defects, for example on an insufflated injured lung with the purpose of realizing contemporary immediate and extended aerostasis and optionally hemostasis. The foil formulation of collagen biomatrix used for this purpose can improve lung function during respiration. The collagens fibrils of the collagen biomatrix can provide a support matrix for substitution and regeneration and facilitate the migration of fibroblasts and repair cells. In some cases, a collagen biomatrix is provided for directed cell ingrowth and de-novo formation of extracellular matrix for the regeneration of visceral and parietal membranes, for example in treating defects of the visceral membrane of the lung following lung decortication.

Embodiments encompass methods of using a substantially nonporous collagen foil to repair and regenerate visceral or parietal tissue, such as pleural tissue, of mammals when the tissue is damaged as a result of injury, tumors, surgery, and the like. The nonporous collagen foil include collagen fibrils which provide a replacement membrane composition that is elastic, liquid-tight and air-tight, and which has a high tensile strength. The nonporous collagen foil is furthermore resorbable and provides a biomatrix, wherein a neo-visceral or neo-parietal membrane, such as a neo-pleura, is rapidly formed which becomes indistinguishable from the autologous membrane, such as an autologous pleura, in a matter of weeks. The process for making the collagen foil can reduce the likelihood of disease transmission.

Embodiments include methods for treating or preventing post-surgical or post-traumatic cellular adhesion on the surface of a tissue such as the pleura, or between a wound surface and the adjacent anatomy, such as between the lung surface and chest wall. Methods may include covering the tissue with a multilayered bioactive and biofunctional collagen biomatrix foil, and directing cell growth and tissue repair. Methods may also include treating a disorder in a mammal by covering the tissue with a multilayered collagen foil biomatrix. Methods are useful for inhibiting or preventing adhesion and scar tissue formation by providing a biofunctional matrix for directed in-growth of cells and controlled tissue regeneration.

Embodiments further encompass methods for treating or inhibiting AALs (Alveolar Air Leaks) or PAALs (Persistent Alveolar Air Leaks).

In one aspect, embodiments of the present invention encompass methods for treating a disorder in a patient characterized by a defect of a visceral or parietal membrane. Methods may include administering to the defect a biofunctional nonporous multilayered collagen foil biomatrix which directs cell growth within interstices of the multilayered collagen foil biomatrix. In some cases, the multilayered collagen foil biomatrix forms a substantially liquid tight and air tight layer between the visceral or parietal defect and an adjacent tissue. In some cases, the administering step includes attaching the multilayered collagen foil biomatrix to the visceral or parietal defect with fibrin sealant, attaching the multilayered collagen foil biomatrix to the visceral or parietal defect with surgical sealant, attaching the multilayered collagen foil biomatrix to the visceral or parietal defect with surgical sutures, utilizing pressure fitting techniques, or utilizing natural adhesion between the multilayered collagen foil biomatrix and the visceral or parietal defect. Optionally, the multilayered collagen foil biomatrix is attached to the visceral or parietal defect of the patient using a fibrin sealant. In some instances, the multilayered collagen foil biomatrix is coupled or coated with a material comprising polyethylene glycol. In some instances, the biomatrix does not promote adhesions with an adjacent tissue after cell growth within interstices of the multilayered collagen foil biomatrix. The multilayered collagen foil biomatrix can direct cell growth on the outer surface of the multilayered collagen foil biomatrix. The multilayered collagen foil biomatrix may include an excipient such as an antibiotic, a preservative, a growth factor, or an additive that aids in the flexibility and elasticity of the multilayered collagen foil biomatrix. In some cases, the multilayered collagen foil biomatrix includes collagen derived from a such as a bovine source, a porcine source, an equine source, an ovine source, a primate source, a rodentia source, or a human source. The multilayered collagen foil biomatrix may include collagen derived from tendon tissue.

In another aspect, embodiments of the present invention encompass methods for regenerating a visceral or parietal membrane in a mammal. Methods may include contacting a defect in the visceral or parietal membrane with a collagen foil. The foil may include a non-naturally occurring biomatrix of multiple layers of collagen fibrils that are not cross-linked by chemicals or radiation. The biomatrix may be substantially nonporous. In some cases, the multilayered collagen foil biomatrix forms a substantially liquid tight and air tight layer between the visceral or parietal membrane and an adjacent tissue. The multilayered collagen foil biomatrix may be attached to the visceral or parietal defect of the patient using a fibrin sealant. The multilayered collagen foil biomatrix may be coupled or coated with a material that includes polyethylene glycol. In some cases, the biomatrix does not promote adhesions with an adjacent tissue after cell growth within interstices of the multilayered collagen foil biomatrix.

In still another aspect, embodiments of the present invention encompass methods for directed cell in-growth and controlled tissue regeneration of a visceral or parietal membrane to prevent post-surgical or post-traumatic adhesion and fibrosis formation on the surface of a tissue in a mammal. Methods may include contacting the tissue with a nonporous microscopically multilayered collagen foil biomatrix. The multilayered collagen foil biomatrix may form a substantially liquid tight and air tight layer between a visceral or parietal membrane defect and an adjacent tissue. The multilayered collagen foil biomatrix may be attached with or to the visceral or parietal membrane defect of the patient using a fibrin sealant. In some cases, the multilayered collagen foil biomatrix is coupled with a material such as polyethylene glycol. In some cases, the biomatrix does not promote adhesions with an adjacent tissue after cell growth within interstices of the multilayered collagen foil biomatrix.

In yet another aspect, embodiments of the present invention encompass the use of a composition in the manufacture of a medicament for the repair of a visceral or parietal defect in a mammal. The composition may include a microscopically multilayered collagen foil biomatrix which directs the growth of cells in interstices between collagen layers of the biomatrix. The multilayered collagen foil biomatrix may form a substantially liquid tight and air tight layer between an organ surface and an adjacent cavity or tissue. The multilayered collagen foil biomatrix may be attached to a visceral or parietal membrane of the patient using a fibrin sealant. Optionally, the multilayered collagen foil biomatrix may be coupled with a material comprising polyethylene glycol. In some cases, the biomatrix does not promote adhesions with an adjacent tissue after cell growth within interstices of the multilayered collagen foil biomatrix. The multilayered collagen foil biomatrix may be smooth and substantially nonporous. Optionally, the multilayered collagen foil biomatrix may be smooth and nonporous. In some cases, the multilayered collagen foil biomatrix is reabsorbed and remodeled into natural tissue. The composition may be provided or available in kit form.

In another aspect, embodiments of the present invention encompass a collagen biomatrix for use in inhibiting post-operative leaks in a visceral or parietal tissue. The collagen biomatrix can be applied post-operatively after resection of the visceral or parietal tissue to prevent or inhibit a tissue leak or an air leak. The collagen biomatrix can recruit fibroblasts and other tissue regenerating cells. In some cases, the collagen biomatrix includes a collagen biomatrix with interstices between collagen layers to permit cell growth in-between the layers. The collagen biomatrix may be applied in conjunction with fibrin sealant. The collagen biomatrix in conjunction with fibrin sealant may prevent or inhibit air leakages up to 28 days after a lung surgery. The fibrin sealant may be applied over the defect with collagen biomatrix applied over or in conjunction with fibrin sealant. In some cases, the areas of the lung tissue covered with a collagen biomatrix regenerate in a more rapid manner than areas of the lung tissue covered with a fibrin sealant.

In one aspect, embodiments of the present invention encompass methods for treating a disorder in a patient characterized by a defect of a visceral pleura. Methods may include the step of administering to the defect a biofunctional nonporous multilayered collagen foil biomatrix which directs cell growth within interstices of the multilayered collagen foil biomatrix. The multilayered collagen foil biomatrix may form a substantially liquid tight and air tight layer between an outer lung surface and a pleural cavity. The administering step may include attaching the multilayered collagen foil biomatrix to the visceral pleura with fibrin sealant, attaching the multilayered collagen foil biomatrix to the visceral pleura with surgical sealant, attaching the multilayered collagen foil biomatrix to the visceral pleura with surgical sutures, utilizing pressure fitting techniques, or utilizing natural adhesion between the multilayered collagen foil biomatrix and the visceral pleura. In some cases, the multilayered collagen foil biomatrix is attached to the visceral pleura of the patient using a fibrin sealant. In some cases, the multilayered collagen foil biomatrix is coupled with a material that includes polyethylene glycol. In some cases, the biomatrix does not promote adhesions with parietal pleura after cell growth within interstices of the multilayered collagen foil biomatrix. The multilayered collagen foil biomatrix may direct cell growth on the outer surface of the multilayered collagen foil biomatrix. The multilayered collagen foil biomatrix may include an excipient such as a preservative, a growth factor, or an additive that aids in the flexibility and elasticity of the multilayered collagen foil biomatrix. The multilayered collagen foil biomatrix may include collagen derived from a source such as a bovine source, a porcine source, an equine source, an ovine source, a primate source, a rodentia source, or a human source. In some cases, the multilayered collagen foil biomatrix includes collagen derived from tendon tissue.

In another aspect, embodiments of the present invention encompass methods for regenerating visceral pleura in a mammal. Methods may include contacting the visceral pleura with a collagen foil having a non-naturally occurring biomatrix of multiple layers of collagen fibrils that are not cross-linked by chemicals or radiation. The biomatrix may be substantially nonporous. The multilayered collagen foil biomatrix may form a substantially liquid tight and air tight layer between an outer lung surface and a pleural cavity. The multilayered collagen foil biomatrix may be attached to the visceral pleura of the patient using a fibrin sealant. The multilayered collagen foil biomatrix may be coupled with an anti-adhesive material such as polyethylene glycol. In some cases, the biomatrix does not promote adhesions with parietal pleura after cell growth within interstices of the multilayered collagen foil biomatrix.

In yet another aspect, embodiments of the present invention encompass methods for directed cell in-growth and controlled tissue regeneration to prevent or inhibit post-surgical or post-traumatic adhesion and fibrosis formation on the surface of a lung tissue in a mammal. Methods may include contacting the lung tissue with a nonporous microscopically multilayered collagen foil biomatrix. The multilayered collagen foil biomatrix may form a substantially liquid tight and air tight layer between an outer lung surface and a pleural cavity. The multilayered collagen foil biomatrix may be attached to the visceral pleura of the patient using a fibrin sealant. In some cases, the multilayered collagen foil biomatrix is coupled or coated with a material that includes polyethylene glycol. In some cases, the biomatrix does not promote adhesions with parietal pleura after cell growth within interstices of the multilayered collagen foil biomatrix.

In still another aspect, embodiments of the present invention encompass the use of a composition in the manufacture of a medicament for the repair of a visceral pleura defect in a mammal. The composition may include a microscopically multilayered collagen foil biomatrix. The multilayered collagen foil biomatrix can direct the growth of cells in interstices between collagen layers of the biomatrix. In some cases, the multilayered collagen foil biomatrix forms a substantially liquid tight and air tight layer between an outer lung surface and a pleural cavity. The multilayered collagen foil biomatrix may be attached to the visceral pleura of the patient using a fibrin sealant. In some cases, the multilayered collagen foil biomatrix is coupled with a material that includes polyethylene glycol. Optionally, the biomatrix may not promote adhesions with parietal pleura after cell growth within interstices of the multilayered collagen foil biomatrix. In some cases, the multilayered collagen foil biomatrix is smooth and substantially nonporous. In some cases, the multilayered collagen foil biomatrix is smooth and nonporous. The multilayered collagen foil biomatrix can be reabsorbed and remodeled into natural tissue. In some cases, the composition is available in kit form.

In some aspects, embodiments of the present invention encompass a collagen biomatrix for use in inhibiting postoperative air leaks in lungs. The collagen biomatrix can be applied post-operatively after pulmonary resection or other lung surgery to prevent air leaks. In some cases, the collagen biomatrix recruits fibroblasts and other tissue regenerating cells. In some cases, the collagen biomatrix includes a collagen biomatrix with interstices between collagen layers to permit cell growth in-between the layers. Optionally, the collagen biomatrix can be applied in conjunction with fibrin sealant. In some cases, the collagen biomatrix in conjunction with fibrin sealant prevents air leakages up to 28 days after surgery. In some cases, the fibrin sealant is applied over the defect with collagen biomatrix applied over or in conjunction with fibrin sealant. In some cases, the areas of the lung tissue covered with the collagen biomatrix regenerate in a more rapid manner than areas of the lung tissue covered with fibrin sealant.

For a fuller understanding of the nature and advantages of the present invention, reference should be had to the ensuing detailed description taken in conjunction with the accompanying drawings.

DETAILED DESCRIPTION OF THE INVENTION

Figure 1:
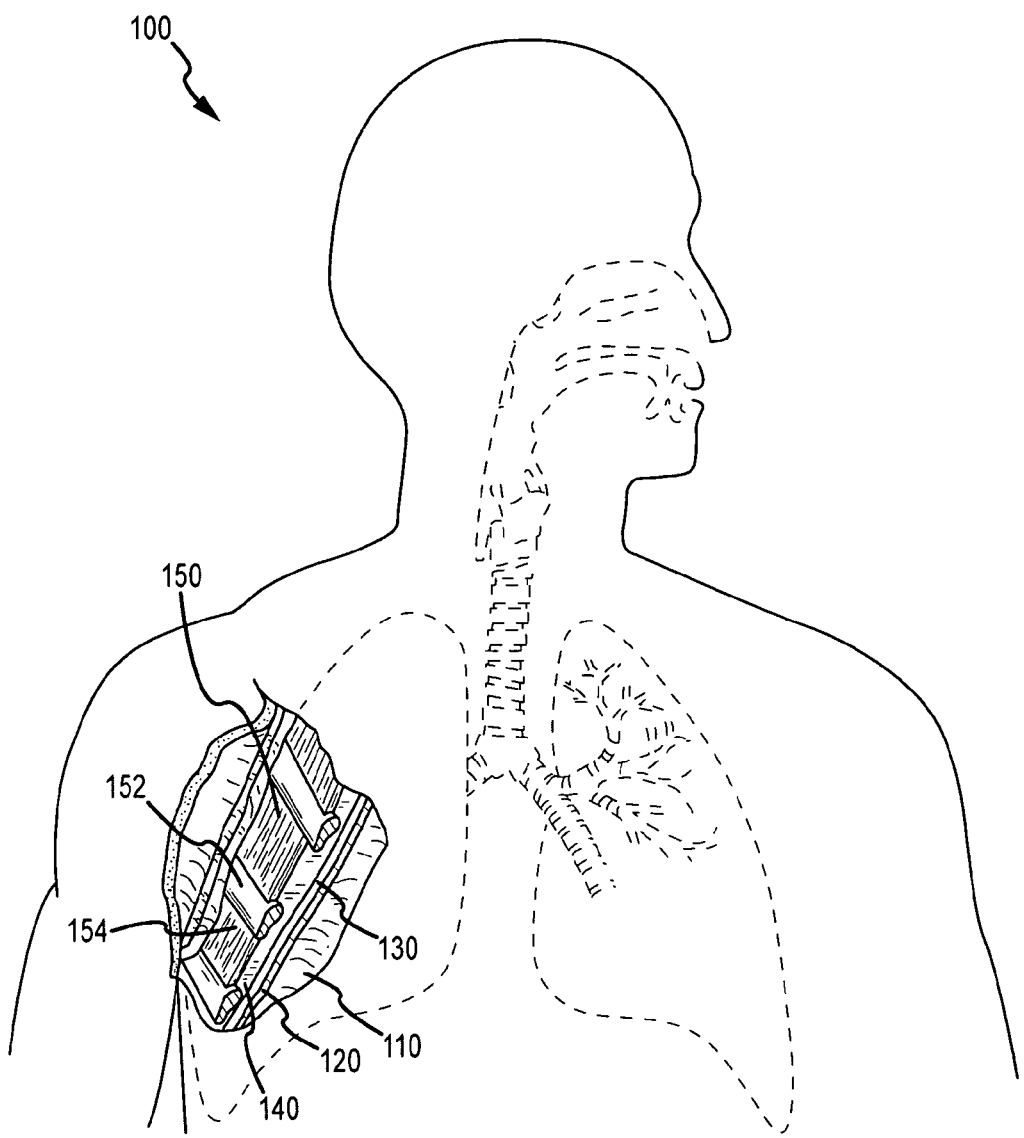
FIG. 1 illustrates selected aspects of patient's thoracic anatomy.

Serous membranes associated with various organs of the body typically include a visceral layer and a parietal layer. Serous cavities include the pericardial cavity which surrounds the heart, the pleural cavity which surrounds the lungs, and the peritoneal cavity which surrounds many abdominal organs. Embodiments of the present invention encompass the use of a collagen biomatrix for the treatment of tissue and visceral or parietal membrane defects or leaks, such as those which may be found in organs such as the lung. The lung is surrounded by a pleural visceral membrane, which is thin delicate serous tissue. Damage to the pleural visceral membrane and lung tissue, for example in conjunction with resections to different degrees (lung resection surgery), can present life-threatening complications for the patient. Postoperative tissue leaks and air leaks are a frequent complication after pulmonary resection for lung cancer or other pathologies in the lung tissue, such as fibrosis and emphysema. Air leaks may cause serious complications, such as empyema, or prolong the need for chest tube and hospitalization. Leakage of air (e.g. from the sutured or stapled surface of lung resections) is known to negatively influence morbidity and mortality after lung surgery.

Exemplary visceral membranes include the visceral peritoneum, the visceral pleura, and the visceral pericardium or epicardium. As suggested above, visceral membranes may surround organs such as the heart, lungs, liver, spleen, gall bladder, and the like. Exemplary parietal membranes include the parietal peritoneum, the parietal pleura, and the parietal pericardium. Defects of such visceral or parietal membranes can lead to unwanted fluid leakage. Visceral or parietal membranes of the lung, liver, kidney, spleen and the thoracic and abdominal cavity have the same or similar wound healing reaction schemes to injuries, resections, damage, and the like, including hemostasis, fibrin formation, fibrin and collagen of the injured tissue as guide rail for wound healing and repair cells, invasion of fibroblasts and repair cells, rebuilding of the extracellular matrix/collagen structure, and vascularisation. The reaction of fibroblasts and repair cells to biofunctional collagen biomatrices disclosed herein may be based on the same or similar principles for many visceral or parietal membrane defects, for example by using properties of the biomatrix in a certain way, such as by directed ingrowth and steering of fibroblasts and repair cells. Embodiments of the present invention encompass techniques for treating visceral or parietal membrane or tissue defects, including techniques for treating parietal and visceral membrane defects or leaks of the lung. Typically, visceral membranes as part of a tissue or organ have epithelial/mesothelial cell layers and other layers and are significantly different from other types of tissues found in the body. According to some embodiments of the present invention, a multilayered, bioactive collagenous biomatrix can be used for the steering of the cell ingrowths and de novo formation of extracellular matrix in visceral membrane regeneration and restoration, such as for pleural visceral membrane regeneration.

Application of Collagen Biomatrix to Patient

Turning now to the drawings, FIG. 1 illustrates relevant aspects of patient's thoracic anatomy. The lung 110 of the patient 100 is adjacent to and covered by a visceral pleura membrane 120. This visceral pleura membrane is attached directly to the lung, and is surrounded by an outer parietal pleural membrane 140 which is adjacent to the chest wall 150 and lines the inside of the thoracic cavity. As shown here, the chest wall 150 includes the ribs 152 and the intercostal muscles 154.

Together, the visceral membrane 120 and parietal membrane 140 make up mesothelium. A pleural cavity 130, sometimes referred to as the intrapleural or interparietal space, is the cavity or space disposed between the visceral pleural membrane 120 and the parietal pleural membrane 140. The parietal layer 140 secretes pleural fluid into the pleural cavity 130, and the pleural fluid is resorbed by the visceral layer 120.

The visceral pleural membrane 120 and the parietal pleural membrane 140 continually tend to pull away from each other because of the stretched elastic condition of the lungs, and maintenance of the intrapleural pressure within the pleural cavity 130 is important for pulmonary ventilation. For example, during inspiration there is a negative pressure within the pleural cavity 130, and during expiration there is a positive pressure within the pleural cavity 130. If the pleura is compromised, air can be sucked into the pleural cavity 130, which may separate the two pleural layers and lead to lung collapse. Accordingly, the visceral pleural membrane 120 and the parietal pleural membrane 140 play an important role in respiration, and air leaks or defects in the membrane and lung tissue can pose a significant risk to the patient.

Relatedly, maintenance of the pleural fluid within the pleural cavity 130 is also important for respiratory functioning of the patient. The fluid lubricates the plane pleural membrane surfaces and helps the lungs move easily relative to the chest wall, for example by reducing friction between the lung and inner surface of the chest wall as the lung expands and contracts during normal breathing. If the visceral pleural membrane 120 or the parietal pleural membrane 140 are damaged and the fluid interface is disrupted, pneumothorax may occur.

Certain pulmonary surgery techniques or injuries may lead to tissue-, air-, or fluid-fluid leakage in a patient's lung. For example, the visceral pleural membrane 120 may become compromised. As noted above, the integrity of pleura plays an important factor in the mechanics of breathing. Collagen biomatrix embodiments described herein, which encourage or steer cell ingrowth into its multilayered plane structure, are well suited for preventing or treating such leaks or defects of the lung and for maintaining or restoring the plane fluid and gas-tight surface of the lung. Due to the elasticity of the collagen biomatrix, it can readily accommodate the movement of lung tissue as the patient breathes.

Figure 2:
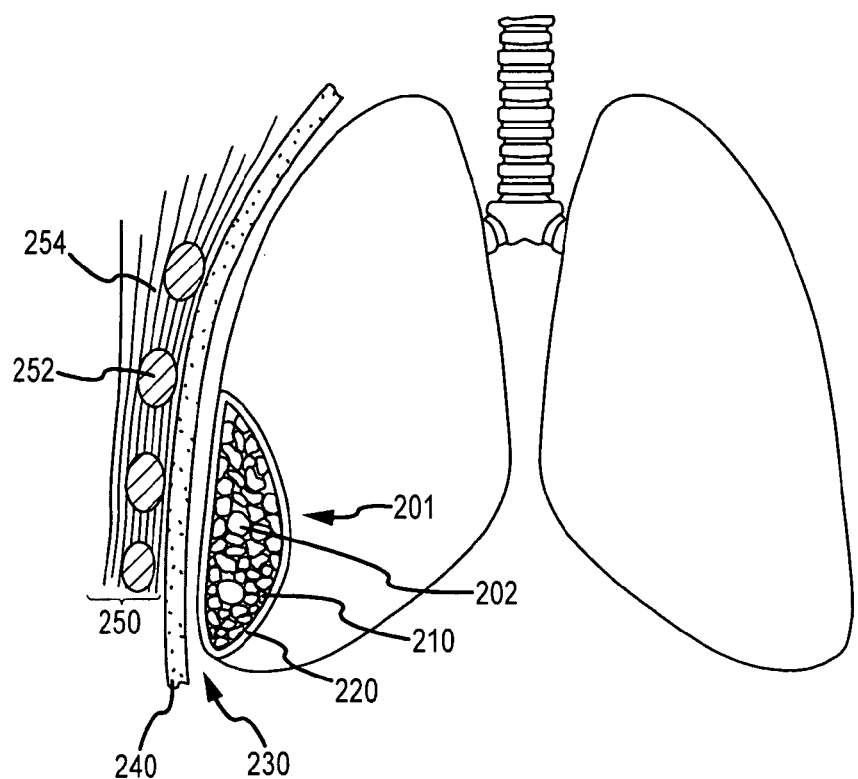
FIG. 2 illustrates selected aspects of a patient's thoracic anatomy and visceral membrane and tissue defects.

FIG. 2 provides another view of the thoracic cavity of a patient. As shown here, the lung tissue 210 is surrounded by the visceral pleura 220, which in turn is surrounded by the parietal pleura 240. The visceral pleural membrane contains several histologic layers. The first layer includes a single layer of mesothelial cells, the second layer includes a submesothelial layer of loose connective tissue, the third layer is an elastic layer of external elastic lamina, the fourth layer is an interstitial or loose connective tissue layer containing lymphatics, large capillaries, and collagen, and the fifth layer includes elastic fibers of internal elastic lamina and fibrous tissue that contacts the lung. The visceral membrane covers the lung parenchyma or tissue and the interlobular fissures. The chest wall 250 includes ribs 252 and muscle 254. FIG. 2 also depicts a lung resection area or defect 201, whereby alveoli or lung tissue 210 is exposed, thus providing pulmonary air leaks 202. Such defects can be created during lung surgery, for example by a surgeon's scalpel, or as a result of injury. As the visceral pleural membrane 220 is removed or compromised, fluid communication between lung tissue 210 and the pleural cavity 230 is established. Removal of the visceral pleural membrane can lead to leakage as the alveoli are ruptured or exposed to the pleural cavity. In some cases, damaged bronchioli may be exposed to the pleural cavity as well. Embodiments of the present invention encompass techniques for sealing or diminishing such fluid communication. For example, fluid leaks 202 can be closed or covered using a collagen biomatrix.

Figure 2A:
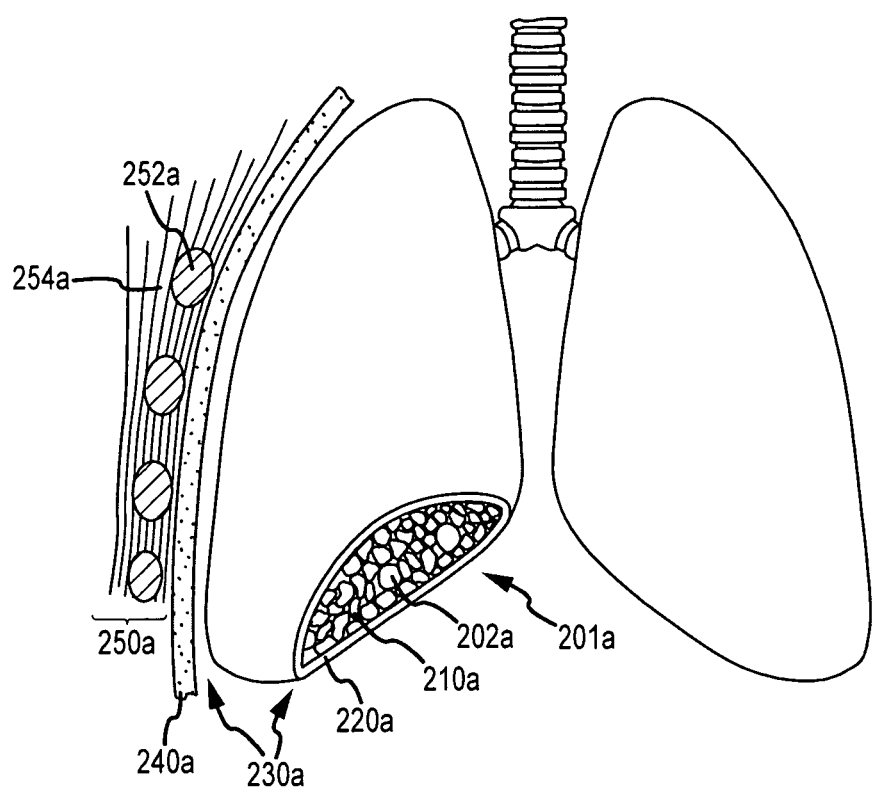
FIG. 2A illustrates selected aspects of a patient's thoracic anatomy and visceral membrane and tissue defects.

FIG. 2A provides still another view of the thoracic cavity of a patient. As shown here, the lung tissue 210a is surrounded by the visceral pleura 220a, which in turn is surrounded by the parietal pleura 240a. The visceral pleura contains several histologic layers. The first layer includes a single layer of mesothelial cells, the second layer includes a submesothelial layer of loose connective tissue, the third layer is an elastic layer of external elastic lamina, the fourth layer is an interstitial or loose connective tissue layer containing lymphatics, large capillaries, and collagen, and the fifth layer includes elastic fibers of internal elastic lamina and fibrous tissue that contacts the lung. The visceral pleura covers the lung parenchyma or tissue and the interlobular fissures. The chest wall 250a includes ribs 252a and muscle 254a. FIG. 2A also depicts a lung resection area or defect 201a, whereby alveoli or lung tissue 210a is exposed, thus providing pulmonary air leaks 202a. Such defects can be created during lung surgery, for example by a surgeon's scalpel, or as a result of injury. As the visceral pleura 220a is removed or compromised, fluid communication between lung tissue 210a and the pleural cavity 230a is established. Removal of the visceral pleura can lead to leakage as the alveoli are ruptured or exposed to the pleural cavity. In some cases, damaged bronchioli may be exposed to the pleural cavity as well. Embodiments of the present invention encompass techniques for sealing or diminishing such fluid communication. For example, fluid leaks 202a can be closed or covered with a collagen biomatrix.

Figure 3:
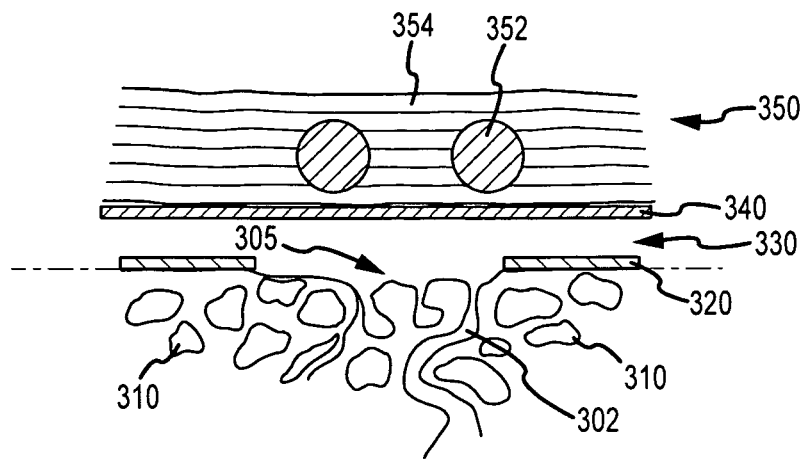
FIG. 3 illustrates aspects of a treatment technique for pleural visceral membrane and lung tissue defects, according to embodiments of the present invention.

FIG. 3 illustrates a defect 305 in the visceral membrane 320. Lung tissue 310 is exposed to the pleural cavity 330 and the parietal pleural membrane 340. As shown here, chest wall 350 includes ribs 352 and muscle 354. Fluid leaks 302 are present between lung tissue 310 and the pleural cavity 330. For example, there may be fluid communication between exposed or damaged alveoli or bronchiole and the pleural cavity. Embodiments of the present invention encompass techniques for sealing or diminishing such fluid communication. For example, fluid or air leaks 302 can be closed or covered with a collagen biomatrix.

Figure 4:
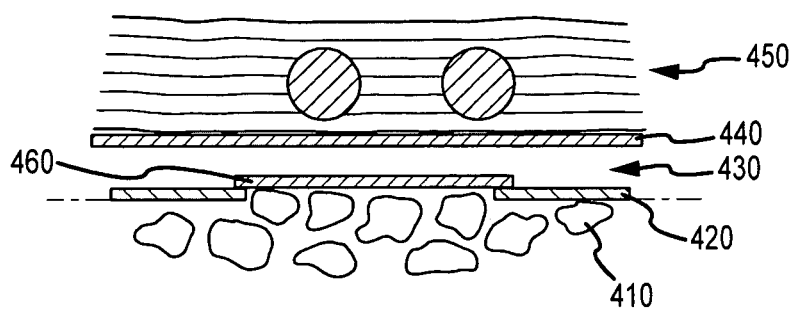
FIG. 4 illustrates aspects of a treatment technique for pleural visceral membrane and lung tissue defects, according to embodiments of the present invention.

As depicted in FIG. 4, a collagen foil biomatrix 460 may be attached to the patient's visceral pleural membrane 420, surface lung tissue 410, or both. The collagen biomatrix slightly overlaps the opening in the patient's visceral membrane to which it is attached. The biomatrix 460 provides a barrier between the lung surface 410 and the pleural cavity 430 or parietal membrane 440, which is adjacent the chest wall 450. In some cases, the natural attraction between the collagen foil biomatrix and visceral membrane or lung surface tissue can be used to attach the collagen foil biomatrix to the visceral membrane or lung surface tissue without the use of any sealant, glue, sutures, or pressure fitting techniques. In some cases, the biomatrix is pre-hydrated, such that once hydrated, the collagen foil can be cut slightly larger than the surgical opening in the patient's visceral membrane. The collagen foil thereby can slightly overlap the opening in the patient's visceral membrane to which it is attached. In one embodiment, the hydrated collagen foil is sized to have an approximately 0.5 cm to about 1 cm overlap with the visceral membrane. The amount of overlap can vary depending on the preferences and skill of the surgeon.

Figure 5:
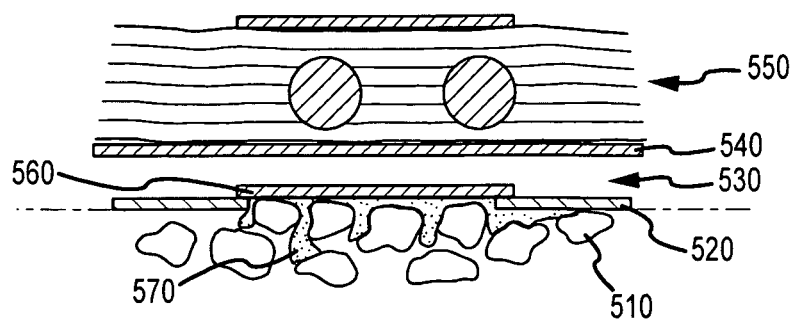
FIG. 5 illustrates aspects of a treatment technique for pleural visceral membrane and lung tissue defects, according to embodiments of the present invention.

As depicted in FIG. 5, a collagen foil or biomatrix 560 may be attached to the patient's visceral membrane 520, surface lung tissue 510, or both, using a fibrin sealant 570. Examples of fibrin sealant approved for surgical use include TISSU-COL™ and TISSEEL™ fibrin sealants (Baxter AG, Vienna, Austria). Alternatively, a surgical sealant that is approved for surgical use may also be utilized. The fibrin sealant or surgical sealant may be applied in a continuous line around the portion of the collagen foil that overlaps the visceral membrane in order to form a liquid-tight and air-tight seal. The collagen foil biomatrix may slightly overlap the opening in the patient's visceral membrane to which it is attached. The biomatrix 560, optionally in conjunction with the fibrin sealant 570, provides a barrier between the lung surface 510 and the pleural cavity 530 or parietal membrane 540, which is adjacent the chest wall 550. As depicted here, the biomatrix is positioned at or near the surface of the lung tissue, and the sealant is disposed more deeply within the lung tissue. Sealant may help to close defects, for example by contributing to a barrier between alveoli or bronchiole and the pleural cavity.

Figure 6:
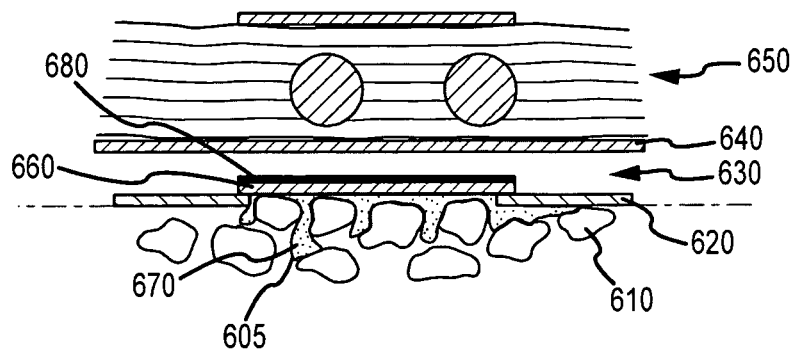
FIG. 6 illustrates aspects of a treatment technique for pleural visceral membrane and lung tissue defects, according to embodiments of the present invention.

In some instances, the collagen foil biomatrix may be utilized in conjunction with other products. For instance, after applying the collagen foil biomatrix to the tissue and securing by any of the means described herein, an anti-adhesion product may be applied to the upper or lower surface of the collagen foil biomatrix, or to adjacent tissues. FIG. 6 illustrates a repair technique for treating a defect 605 in the visceral membrane 620 with a collagen foil or biomatrix 660. Optionally, the collagen biomatrix 660 can be treated or combined with an anti-adhesion material 680, such as polyethylene glycol (PEG). For example, PEG can be applied to, incorporated into, coupled with, or coated on a surface of the biomatrix, and can operate as a separating layer between the biomatrix 660 and the surrounding tissue. When the biomatrix is applied to the patient, the surface with PEG can be placed facing toward the chest wall 650. Fibroblasts coming from the lung surface can migrate into the biomatrix, and the PEG can prevent or inhibit adhesion formation between the lung surface and parietal pleura 640 or chest wall. Hence, a PEG based product may be applied to the upper or lower surfaces, or both, of the collagen foil biomatrix, or to adjacent tissues. In some cases, a PEG-precoated collagen biomatrix can be used. As the collagen foil biomatrix prevents adhesion by directing tissue regeneration, rather than by creating a "slippery" surface, its action may be complemented by utilizing products that temporarily create a "slippery" surface to which cells will not adhere. In another embodiment a ready-to-use collagen foil biomatrix, which is already coated with a PEG-based product on one or both surfaces may be used. Optionally, the biomatrix 660 may be attached to the patient's visceral pleura 620, surface lung tissue 610, or both, using a fibrin sealant 670. The biomatrix 660, optionally in conjunction with the fibrin sealant 670, provides a barrier between the lung surface 610 and the pleural cavity 630 or parietal pleural membrane 640, which is adjacent the chest wall 650. A PEG layer may provide a separation layer, facing toward the parietal membrane, and may also provide a slippery surface allowing movement of pleural membranes. A PEG layer may also be dissolved and resorbed quickly. The collagen biomatrix can provide a multilayered bioactive regenerative material that directs cell ingrowth and enhances regeneration of a laminar visceral membrane. The sealant, optionally including fibrinogen and thrombin, can allow fixation, fill small gaps, and support wound healing and cell attachment and ingrowth on the order of days or weeks. As shown here, the sealant faces toward the injured tissue.

Figure 6A:
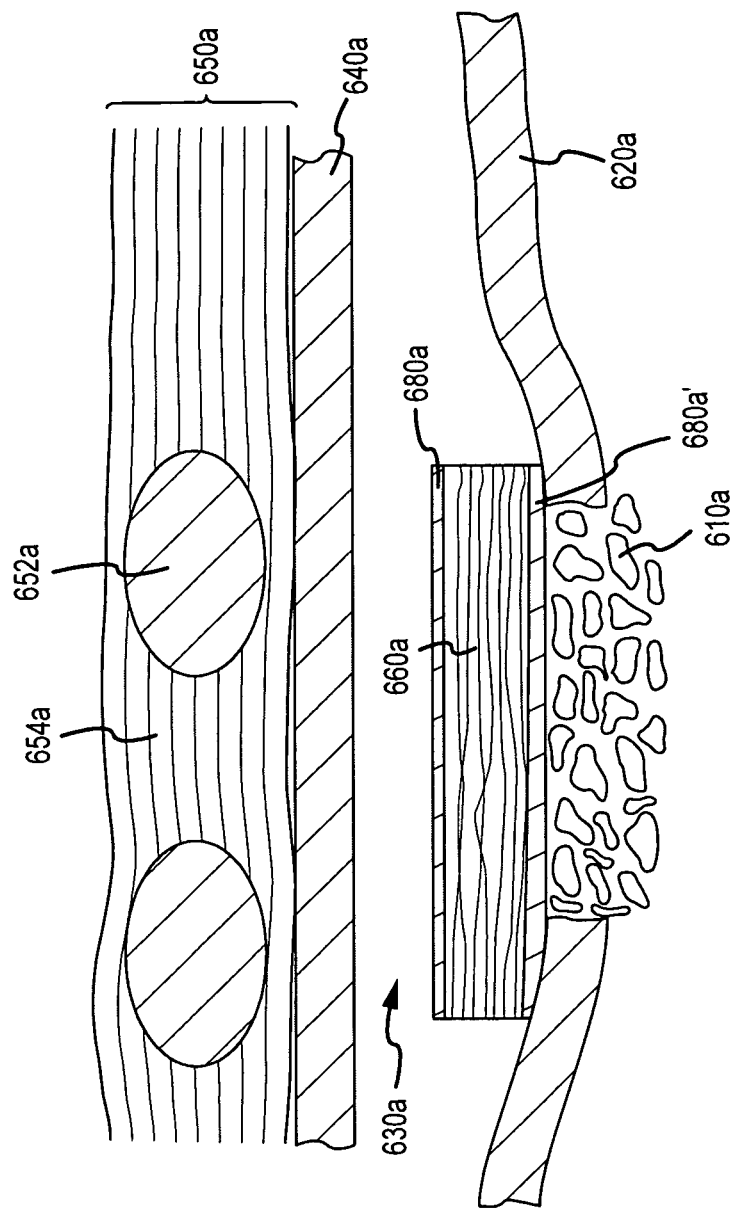
FIG. 6A illustrates aspects of a treatment technique for pleural defects, according to embodiments of the present invention.
Figure 6B:
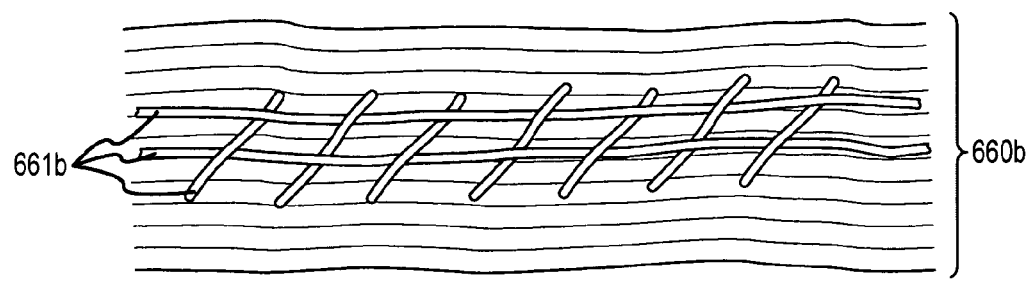
FIG. 6B illustrates aspects of a collagen biomatrix for treating a visceral membrane defect, according to embodiments of the present invention.
Figure 7:
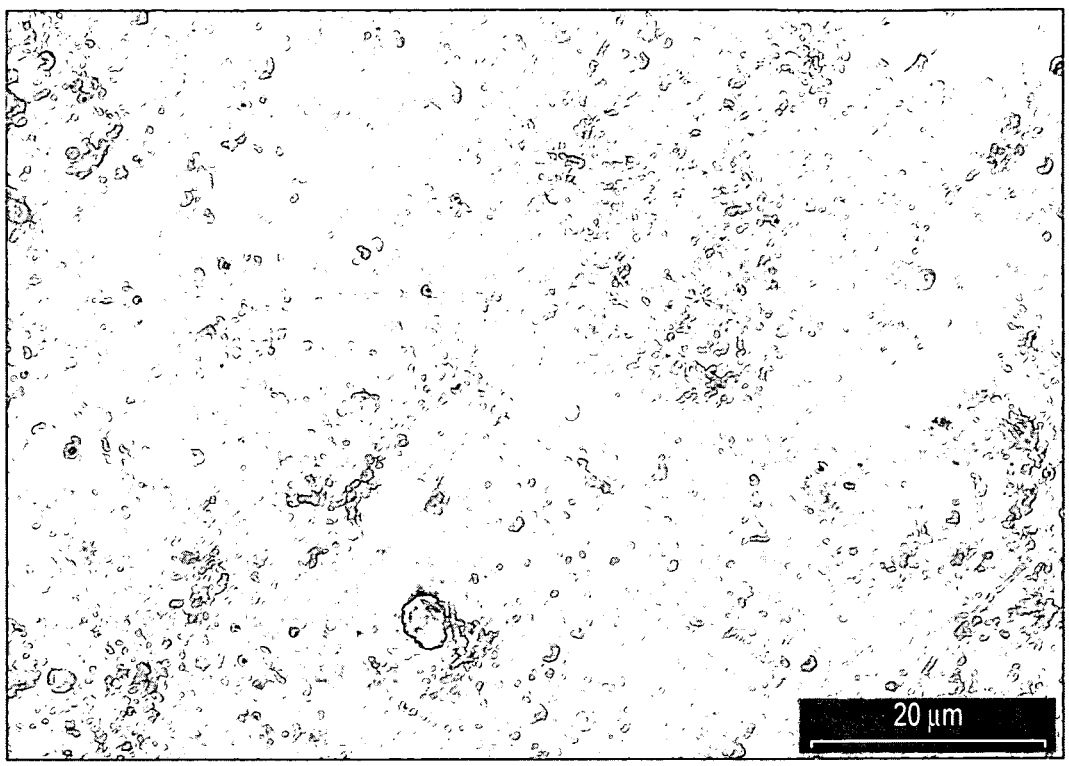
FIG. 7 is a SEM (scanning electron microscope) photograph illustrating the primarily poreless or nonporous fluid- and air-tight surface of a biofunctional collagen foil biomatrix according to embodiments of the present invention.

In some instances, an anti-adhesion product may be applied to both the upper and lower surfaces of the collagen foil biomatrix. FIG. 6A illustrates a repair technique for treating a defect 605a in the visceral pleura 620a with such a collagen foil or biomatrix 660a. Chest wall 650a includes ribs 652a and muscle 654a. As depicted here, the collagen biomatrix 660a is treated or combined with an anti-adhesion material 680a, such as polyethylene glycol (PEG), on one side of the biomatrix, and is also treated or combined with an anti-adhesion material 680b, such as polyethylene glycol (PEG), on the other side of the biomatrix. The anti-adhesion material 680a, 680b can provide a separating layer between the biomatrix 660a and the surrounding tissue. When the biomatrix is applied to the patient, one surface with PEG can be placed facing toward the parietal membrane 640a or chest wall 650a, and the other surface with PEG can be placed facing toward the lung tissue 610a. In some embodiments, the slippery outer PEG coating 680a can enhance undisturbed movement of the pleura visceralis and the parietalis during breathing, and can also help to provide a temporary closure of injuries and a viscose separation layer. The collagen biomatrix 660a can provide for directed cell ingrowth and enhanced regeneration and reconstruction of a sound, normal tissue, e.g. restitution ad integrum. The inner PEG coating 680a' can be placed facing toward lung tissue having air leaks. Inner PEG coating 680a' can fill small gaps in the lung tissue, 610a, and can be quickly hydrolyzed and resorbed, for example within hours, and allow undisturbed physiological wound healing within, for example, days and weeks. Such a double sided PEG coated biomatrix can offer simple handling, because the biomatrix may be applied right side up, or upside down. FIG. 6B illustrates an exemplary multilayered collagen biomatrix 660b having a surgical mesh 661b, which may provide for enhanced stability and suturability of the biomatrix. Surgical mesh 661b can include any of a variety of surgical fabrics or felts, and may include materials such as polypropylene, polyester, polytetrafluoroethylene, and the like.

Prior to use, the dry collagen foil may be hydrated, e.g., in physiological saline. In one embodiment, the physiological saline includes a 0.9% sodium chloride solution. In another embodiment, the collagen foil is hydrated in excipients or drug-containing solutions. The length of time necessary to hydrate the collagen foil may be related to the thickness of the foil. The collagen foil can be hydrated until it is consistent in thickness across its entire area. The collagen foil biomatrix may be resistant to disintegration in water or physiological saline solutions. In one embodiment the collagen foil is hydrated between about 1 second and about 1 hour in physiological saline. In another embodiment, the collagen foil is hydrated between about 1 second and about 30 minutes in physiological saline. In another embodiment, the collagen foil is hydrated between about 1 second and about 20 minutes in physiological saline. In another embodiment, the collagen foil is hydrated between about 1 second and about 10 minutes in physiological saline. In still another embodiment, the collagen foil is hydrated between about 1 minute and about 6 minutes in physiological saline. In another embodiment, the collagen foil is dipped into the physiological saline and immediately removed. Such semi-hydration can lead to enhanced adherence to tissues. In another embodiment, the collagen foil is hydrated about 5 minutes in physiological saline. In another embodiment, the collagen foil is not hydrated prior to implantation, which can provide immediate adherence at application to tissues and hydration in situ.

Embodiments of the present invention encompass the use, manufacture, or application of multilayered collagen foil biomatrices, such as those described in WO 2004/108179 or WO 2007/137839, the contents of which are incorporated herein by reference. As noted above, a biomatrix may be used in conjunction with fibrin sealant. In some cases, fibrin sealant may be applied to a treatment site or location prior to application of the biomatrix. In some cases, fibrin sealant and the biomatrix can be applied together. Fibrin sealants typically include two main active components: fibrinogen and thrombin. The thrombin helps to convert the fibrinogen into fibrin monomers, which can cross-link to form a fibrin matrix, which can link to the injured tissue, such as pulmonary tissue, and to the native collagen fibrils of the collagen biomatrix. A fibrin glue may include an autologous fibrin sealant, derived from the patient's own serum. In some cases, collagen biomatrix is applied in combination with fibrinogen, followed by application of thrombin. In some cases, fibrinogen is applied, followed by application of the collagen biomatrix in combination with thrombin. In some cases, collagen biomatrix is applied in combination with fibrinogen and thrombin. Fibrin sealant can be applied to a surface of the biomatrix, for example on a side of the biomatrix which faces afterwards toward the lung surface upon application of the biomatrix to the patient. The fibrin sealant can help fix or adhere the biomatrix to the patient's lung tissue. In some cases, fibrin sealant can at least partially fill gaps between a rough surface of the lung tissue and the biomatrix. Hence, the sealant can facilitate close contact between the biomatrix and the lung surface and support cell attachment and cell growth. Fibrin sealant may be applied to a collagen biomatrix in a thin layer. Fibrin sealant may also provide barrier properties, for example against fluids and gases.

Optionally, a collagen biomatrix, or a component associated with the biomatrix such as a PEG layer or fibrin sealant layer, can be treated with or include a coloring agent, to allow an individual to discern one side of the biomatrix from the other. For example, one side of a biomatrix that includes a fibrin sealant for fixation can have a coloring agent or dye such as methylene blue. Such visual markers can assist a surgeon in determining how to apply the biomatrix to a patient. In the example noted above, the surgeon could apply the biomatrix so that the blue side faces toward the lung surface.

As part of a surgical procedure, a surgeon or other healthcare professional can apply a rinse to the biomatrix. For example, a surgeon may hydrate the biomatrix with a saline solution prior to application of the biomatrix to the patient tissue. Upon application to the patient, the natural fluid between lung and chest wall can also provide hydration to the biomatrix. In some cases, a surgeon can apply the biomatrix to the patient, and can peel off and reposition the biomatrix as needed. Such techniques may be facilitated with an adequately hydrated biomatrix. Hydration can also be performed with solutions, when the biomatrix is already in situ.

In another embodiment, the collagen foil produces a liquid-tight and air-tight seal when attached to the autologous visceral pleura or lung surface with or without a continuous line of fibrin sealant or surgical sealant. In another embodiment, the collagen foil that overlaps the visceral pleura or lung surface can be dotted with fibrin sealant or surgical sealant to attach it to the visceral pleura or lung surface. A liquid-tight seal fixation may be advantageous as it avoids complications associated with contact of the adjacent tissues with hemorrhages, e.g., induction of adhesion formation by uncontrolled bleeding and fibrin exudation. In another example the collagen foil biomatrix produces a liquid-tight and air-tight seal when attached to the tissue with a continuous line of fibrin sealant or surgical sealant. In a further example the collagen foil biomatrix that overlaps the tissue can be dotted with fibrin sealant or surgical sealant to attach it to the tissue. In still another example the collagen foil biomatrix is attached by surgically suturing it to the tissue once it has been positioned to the desired contact site. If the collagen foil biomatrix is to be sutured, tensionless suturing techniques can be used to prevent tearing the foil. It may be desirable to seal suture lines, for example, with a fibrin sealant. In another example, the collagen foil biomatrix is positioned and implanted according to known pressure fitting techniques. In some techniques, the collagen foil biomatrix is positioned in the desired implantation site and held in place by the surrounding tissues. Thus, the graft remains in place without the use of surgical sutures, fibrin sealant, or surgical sealant glue. In another example, the collagen foil biomatrix is positioned and implanted without the use of any sealant, glue, sutures, or pressure fitting techniques. In this technique, the collagen foil biomatrix is positioned in the desired implantation site and held in place by the natural attraction or adhesion that occurs between the collagen foil biomatrix and the mammalian tissue. In another example, semi-hydration of the biomatrix can enhance the adherence to injured wettish tissue. In another example, the collagen foil biomatrix may be applied to a tissue and affixed by any of the methods described herein, and then another collagen foil biomatrix may be applied to an adjacent tissue, and applied by any of the methods described herein, thus resulting in adjacent sheets of the collagen foil biomatrix.

In another embodiment, the collagen foil is attached by surgically suturing it to the injured tissue, e.g. the visceral pleura, once it has been positioned to the desired implantation site. This embodiment may be utilized to attach the collagen foil to the autologous visceral pleural membranes of the patient. If the collagen foil is to be sutured, tensionless suturing techniques may be used to prevent tearing the foil. Suture lines may be sealed, for example, with a fibrin sealant.

In another embodiment, the collagen foil is positioned and implanted according to pressure fitting techniques. In this technique, the collagen foil is positioned in the desired implantation site and held in place by the natural internal pressure present in the respective anatomy. Thus, the graft can remain in place without the use of surgical sutures, fibrin sealant, or tissue glue.

In another embodiment, the collagen foil is positioned and implanted without the use of any sealant, glue, sutures, or pressure fitting techniques. In this technique, the collagen foil is positioned in the desired implantation site and held in place by the natural attraction or adhesion that occurs between the collagen foil and the injured tissue, e.g. parenchyma.

The collagen foil can be utilized as a temporary replacement visceral membrane graft to repair human visceral tissue, e.g. visceral pleural tissue, due to a congenital condition, birth defect, disease, injury, tumor removal or other surgical procedure that disrupts or penetrates the visceral membrane of a patient, or any other condition which may benefit from the repair of visceral membrane, e.g. visceral pleura. The collagen foil may also be utilized to repair visceral membrane tissue of any of a variety of mammals, including, but not limited to sheep, monkeys, horses, rats, mice, humans, laboratory animals, or other mammals. Embodiments of the present invention are further directed to kits having collagen foil and instructions for its preparation and use as a replacement visceral membrane.

Methods of covering the tissue with a multilayered biofunctional collagen foil biomatrix may be carried out during the treatment of any injuries or defects of visceral membranes. In some cases, the step of applying the matrix to the patient can be performed during or as part of a lung surgery. In some cases, the multilayered collagen foil biomatrix can attract cells such as repair cells and regeneration cells and direct their in-growth along the multiple bioactive layers and through and on the foil biomatrix. The multilayered collagen foil biomatrix can be reabsorbed and remodeled to natural tissue by the in-growth of cells. The layerstructured collagen foil biomatrix can act as a bioactive and biofunctional scaffold for cellular in-growth in vivo and is replaced by mammalian tissue with layerstructured autologous collagen during regeneration and restoration. The collagen foil biomatrix can be resorbable by the mammal in which it is implanted. This property may be enhanced by the biofunctionality of the native cross-linked collagen fibers and the multilayered structure of the collagen foil biomatrix, as shown in FIGS. 11A-C and 12A-B for example.

According to some embodiments, the phrase "covering the tissue with a multilayered collagen foil biomatrix" means, in general, bringing the tissue into physical contact with a multilayered collagen foil biomatrix. In some embodiments, the contacting of the tissue with a multilayered collagen foil biomatrix results in an implantation of the foil. Examples of the positioning of the multilayered collagen foil biomatrix are illustrated in FIGS. 3-6 and 14. According to some embodiments, a collagen biomatrix is applied over a defect (overlay). According to some embodiments, a collagen biomatrix is applied under a defect (underlay).

Collagen biomatrix products provide many useful properties. The chemotactic interaction in which they engage facilitates rapid infiltration of endothelial cells and fibroblasts, which in turn produce and deposit new collagen autologous fibres in layers; a concomitant limited lymphocytic inflammatory response in surrounding structures promotes absorption of the collagen biomatrix. Collagen also possesses haemostatic properties which are put to therapeutic use. Platelets deposit themselves on the collagen structure, disintegrate and in doing so release clotting factors which facilitate fibrin formation in conjunction with plasma factors.

Collagen Biomatrix

According to some embodiments, the phrase "multilayered collagen foil biomatrix" or "collagen biomatrix" or "collagen foil" means a biomatrix (e.g. a matrix of biocompatible and biofunctional material) of native collagen fibrils treated to remove non-collagenous components and to form a sheet of collagen fibrils with a multilayered laminar structure on a microscopic level. A multilayered collagen foil may be from any source, such as bovine, ovine, porcine, equine, or human origin treated to remove non-collagenous components and to form a sheet of collagen fibrils, with the same physical characteristics. A collagen foil biomatrix according to some embodiments is substantially nonporous, as determinable by scanning electron microscopy.

According to some embodiments, the term "biofunctional" as used herein in the context of a biofunctional multilayered foil biomatrix means that the biomatrix consists of native collagen fibrils that are recognized and utilized by the cells of an animal in a manner similar to the native collagen fibrils in the animal. For example, without limitation, such functions may include migration of repair and regeneration cells along the biofunctional collagen fibrils and the multi-layered structure, and the deposition of new extracellular matrix by the cells including, or replacing, the biofunctional collagen fibrils.

According to some embodiments, the phrase "non-naturally occurring biomatrix" as used herein means a manufactured matrix or framework having native collagen fibrils formed from (i) a material existing in nature (i.e. natural material) that has been treated or processed in a manner in which the collagen fibrils contained in the natural material have been moved or repositioned from their naturally-occurring arrangement within the collagen structure of the natural material; or (ii) a material not existing in nature (i.e. a non-natural, artificial material, such as a recombinant material) treated or processed to manipulate the arrangement of the collagen fibrils. For example, a non-naturally occurring biomatrix may be formed from starting material which includes collagen that has been mechanically or chemically processed (e.g. grounded, chopped, etc.). A collagen biomatrix that is formed from the treatment or processing of starting material in a manner that preserves the structure of the naturally occurring collagen framework is not a non-naturally occurring biomatrix (e.g. epidermal tissue treated to remove cellular components while preserving the naturally occurring collagen structure).

In some embodiments, the collagen foil biomatrix includes connective tissue proteins having collagen fibrils. For example, the collagen foil biomatrix may include connective tissue proteins with Type I collagen fibrils. In addition to having collagen fibrils, a collagen foil biomatrix can also include an excipient, a preservative, a growth factor, or an additive that aids in the flexibility and elasticity of the final product. Each layer of collagen fibrils can be substantially nonporous. According to some embodiments, the phrase "substantially nonporous" means that any pores that are present in a collagen foil biomatrix as a result of precipitation of collagen fibrins to form a collagen sheet are primarily isolated from one another, and the pores are not interconnected in a manner that traverses the thickness of the collagen foil. Mechanical perforations that create holes in the collagen foil biomatrix are not pores. In some cases, the material appears to be substantially free of pores that would be visible using a scanning electron microscope at 1500× magnification. Scanning electron microscope pictures illustrate the nonporous nature of the collagen foil biomatrix as in FIGS. 7, 8A-B, 9A-B, and 10.

According to some embodiments, the collagen foil is resorbable by the mammal in which it is implanted. Without being bound by any particular theory, it is thought that this property may be enhanced by the structure of the collagen foil. The process utilized to produce the equine collagen foil forms stacked layers of collagen fibrils. Between each layer are interstices into which cells and vasculature of the patient can migrate and form visceral or parietal membrane tissue, such as neo-pleura tissue. Each layer of collagen fibrils can be substantially nonporous. The few pores which may be present are typically isolated from one another and do not interconnect through multiple layers of collagen fibrils. The multiple layer structure of the present invention enhances the liquid-tight and air-tight characteristics of the collagen foil.

Figure 8A:
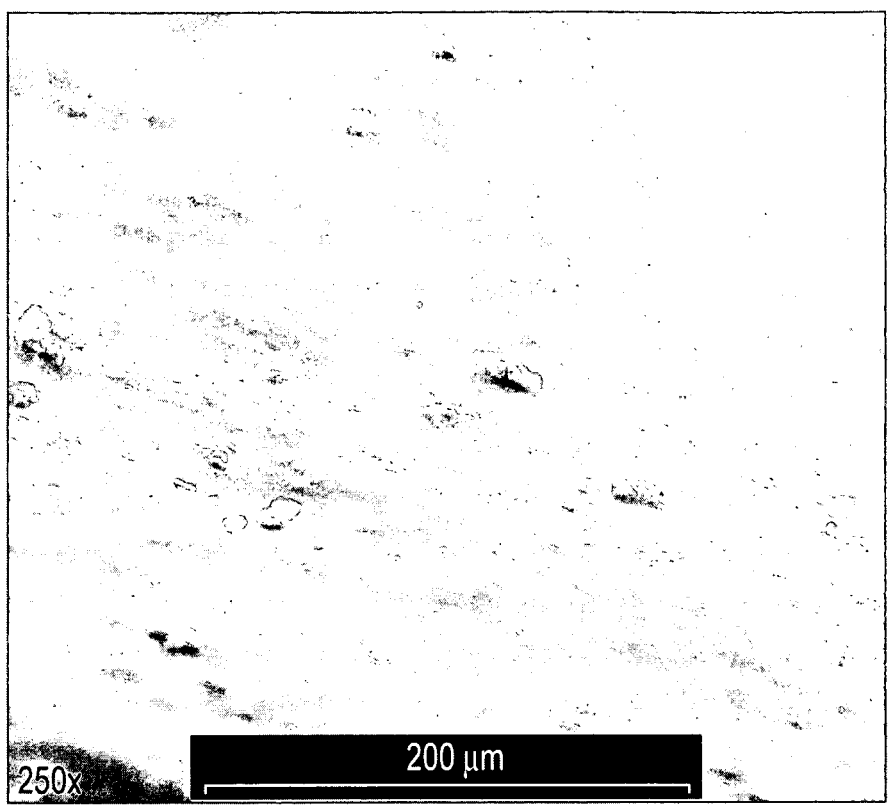
FIGS. 8A and 8B are photographs taken under ESEM (environmental scanning electron microscopy) conditions, which means near natural conditions in a slightly humid atmosphere, illustrating the upper surface, seen from the side of a biofunctional collagen foil biomatrix according to embodiments of the present invention.
Figure 8B:
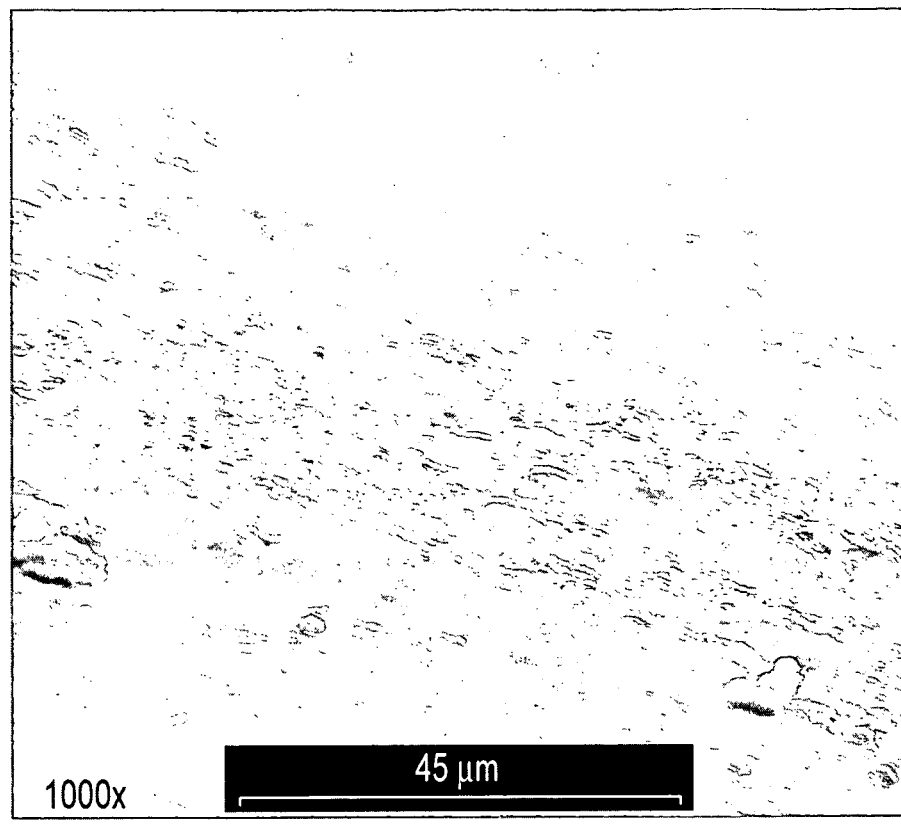
Figure 9A:
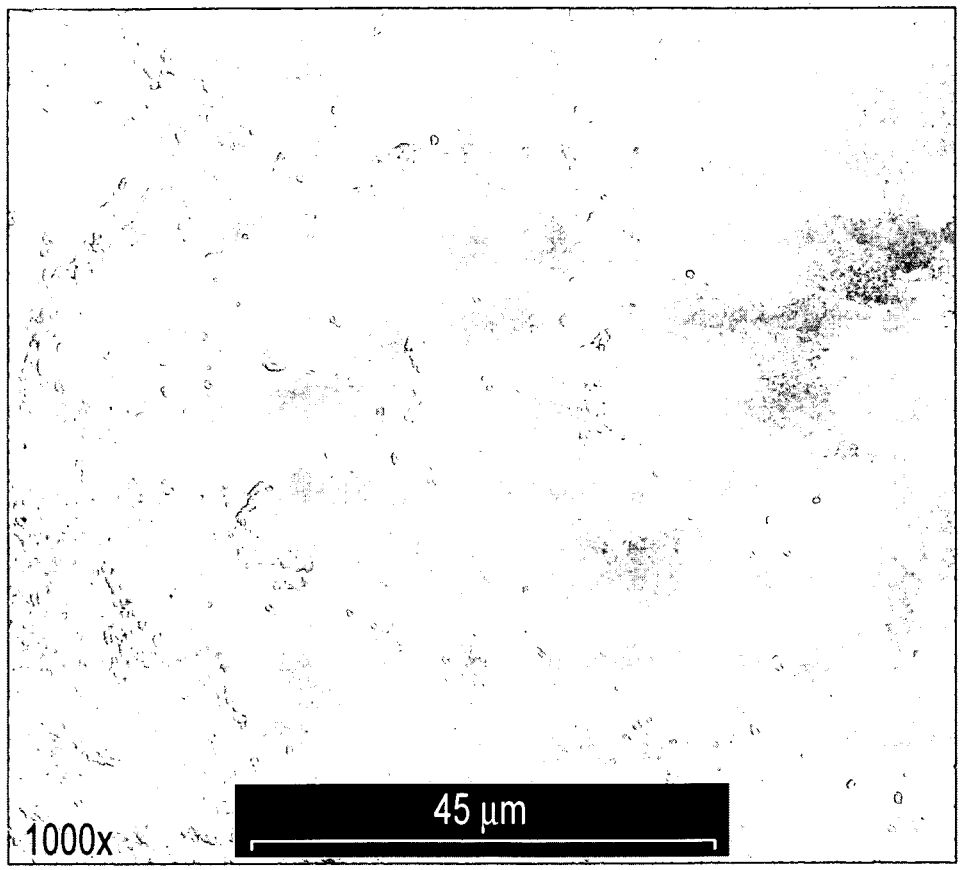
FIGS. 9A and 9B are photographs taken under ESEM conditions illustrating the lower surface of a biofunctional collagen foil biomatrix according to embodiments of the present invention.
Figure 9B:
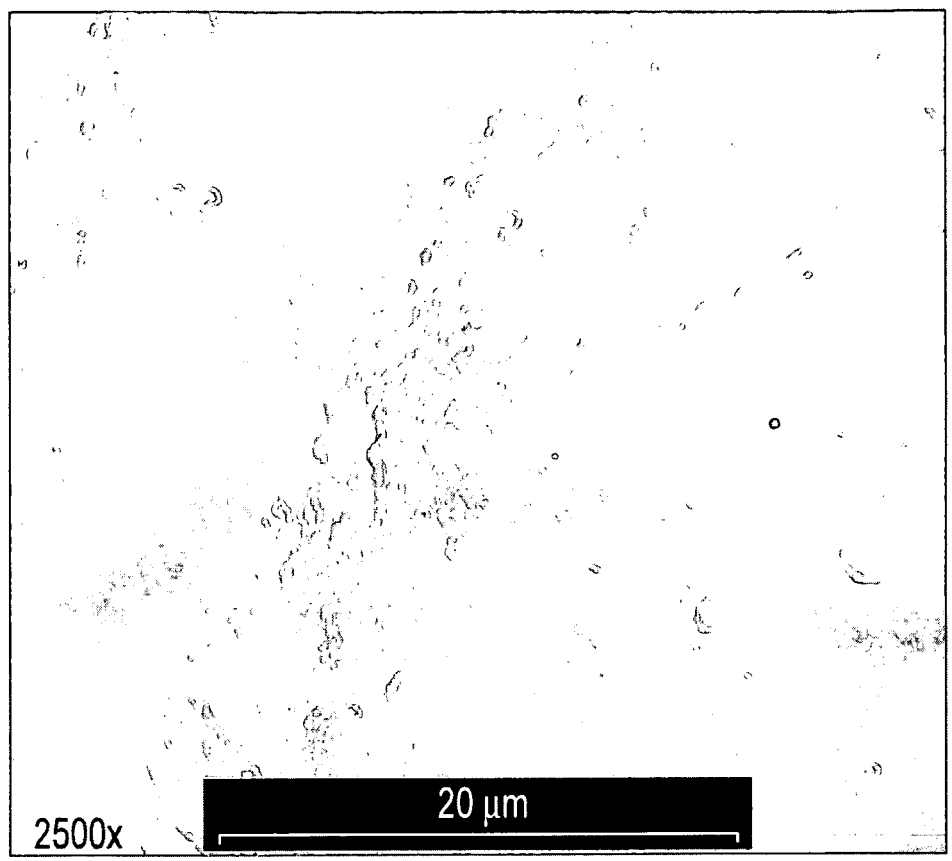

Collagen foil biomatrix embodiments can encompass a non-naturally occurring multi-layered collagen membrane having layers of numerous multi-directional intertwined collagen fibrils. Thus, the collagen fibrils can be arranged in a multi-directional fashion in a plane, and these planes form sheets, which create a multi-layered structure. An illustration of a dry collagen foil biomatrix may be seen in the photomicrograph (SEM) of FIG. 7, which illustrates the surface of the collagen foil biomatrix in which collagen fibrils are embedded. The collagen fibrils are visible on the surface on photographs of the upper surface of the collagen foil biomatrix under ESEM (Environmental Scanning Electron Microscopy) conditions, in which a slightly humid atmosphere provides near natural conditions. As shown in FIGS. 8A-B, the surface appears smooth and substantially nonporous. Photographs (ESEM) of the lower surface of collagen foil biomatrix illustrate the substantial non-porosity of the collagen foil biomatrix, as depicted in FIGS. 9A-B. Collagen fibrils are evident.

The unique orientation of the native collagen fibrils in two-dimensional directions in the multiple layers is primarily responsible for a liquid-tightness and air-tightness, even for example under high hydrostatic pressure, and provides great strength with high elasticity. Due to the numerous parallel-oriented thin collagen fibril layers of the collagen foil biomatrix, this material is suitable for temporarily replacing the body's own visceral or parietal membranes in closing the defect after covering and provides a biofunctional biomatrix scaffold for cell in-growth for forming a new tissue and collagen structures. The multiple layer structure can enhance the liquid-tight and air-tight characteristic of the collagen foil biomatrix.

Figure 10:
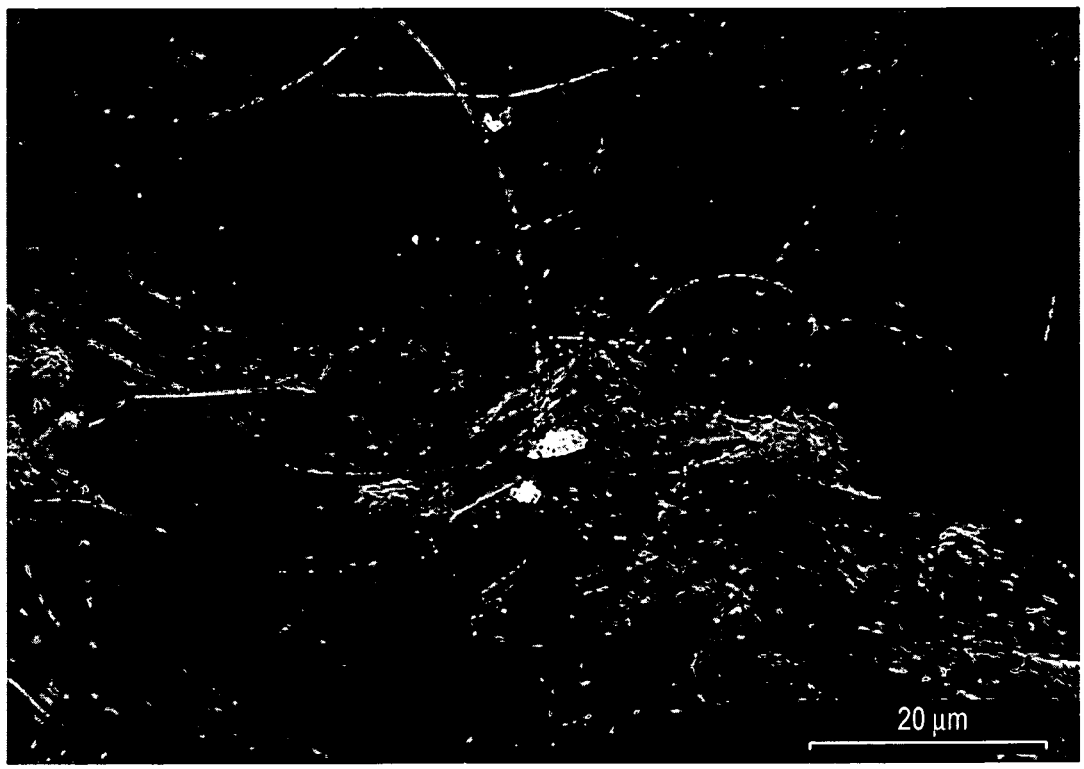
FIG. 10 is a SEM photograph illustrating the surface of a hydrated biofunctional collagen foil biomatrix according to embodiments of the present invention.
Figure 11A:
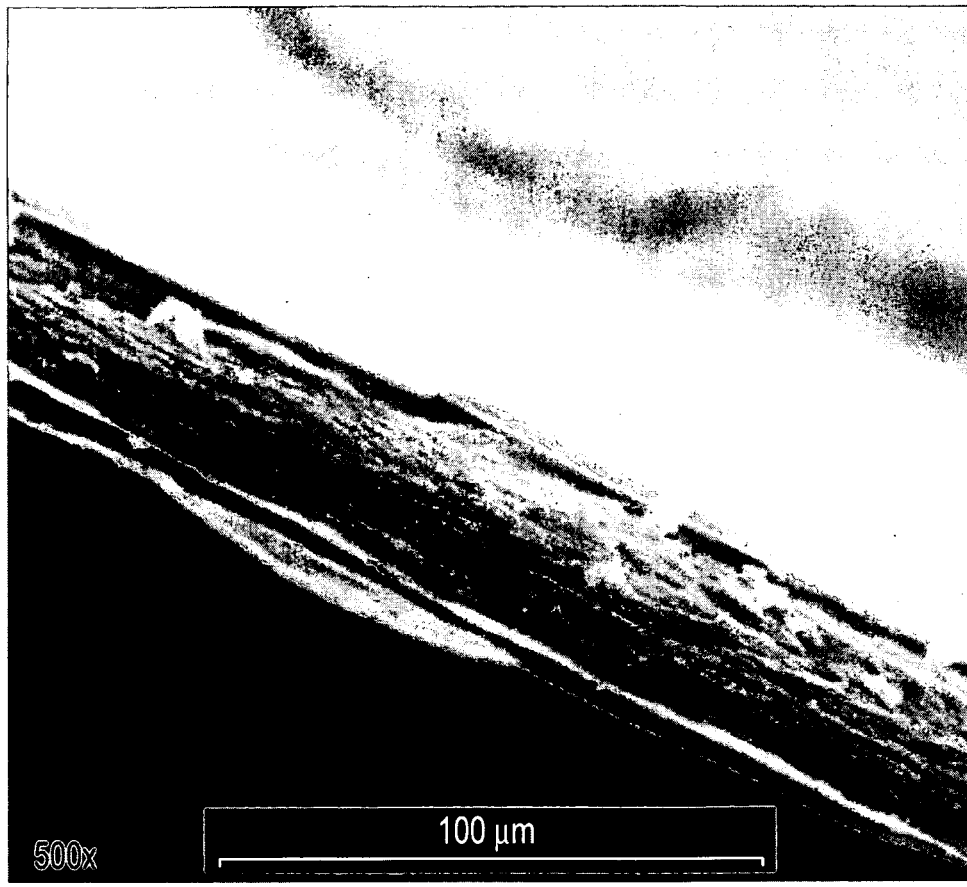
FIGS. 11A, 11B, and 11C are photographs taken under ESEM conditions (humid atmosphere) illustrating the cross section of a biofunctional collagen foil biomatrix according to embodiments of the present invention.
Figure 11B:
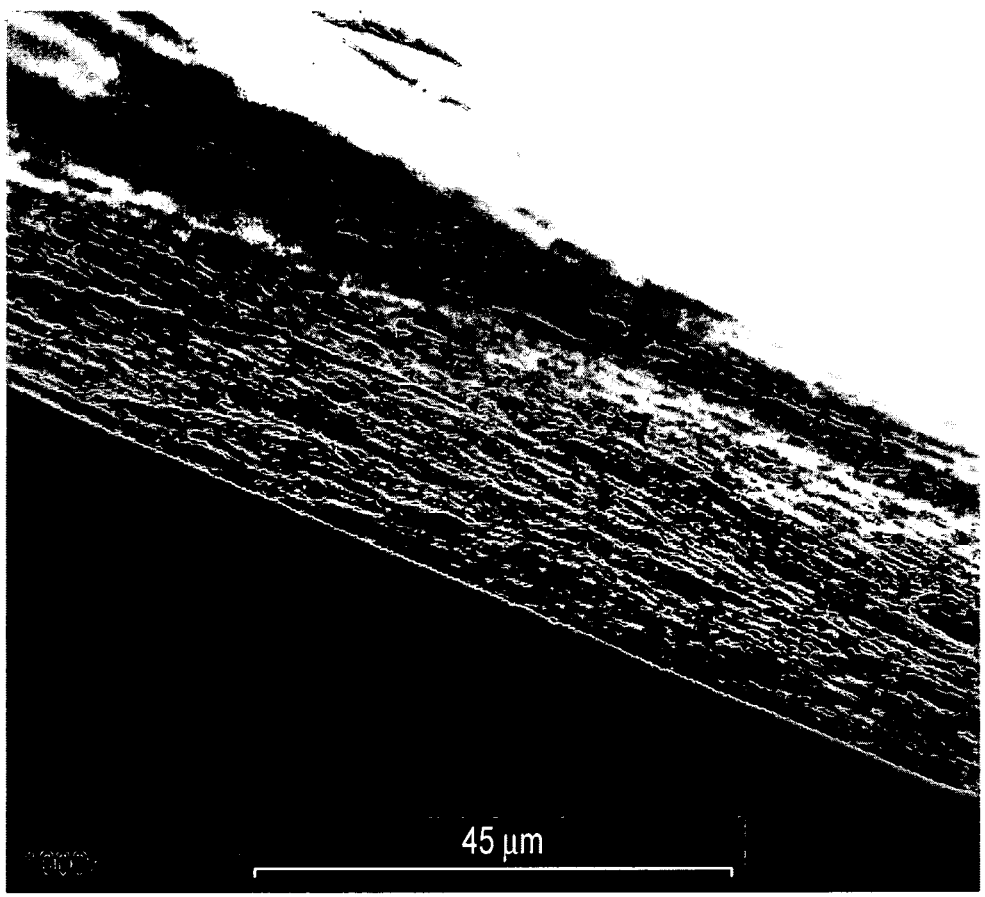
Figure 11C:
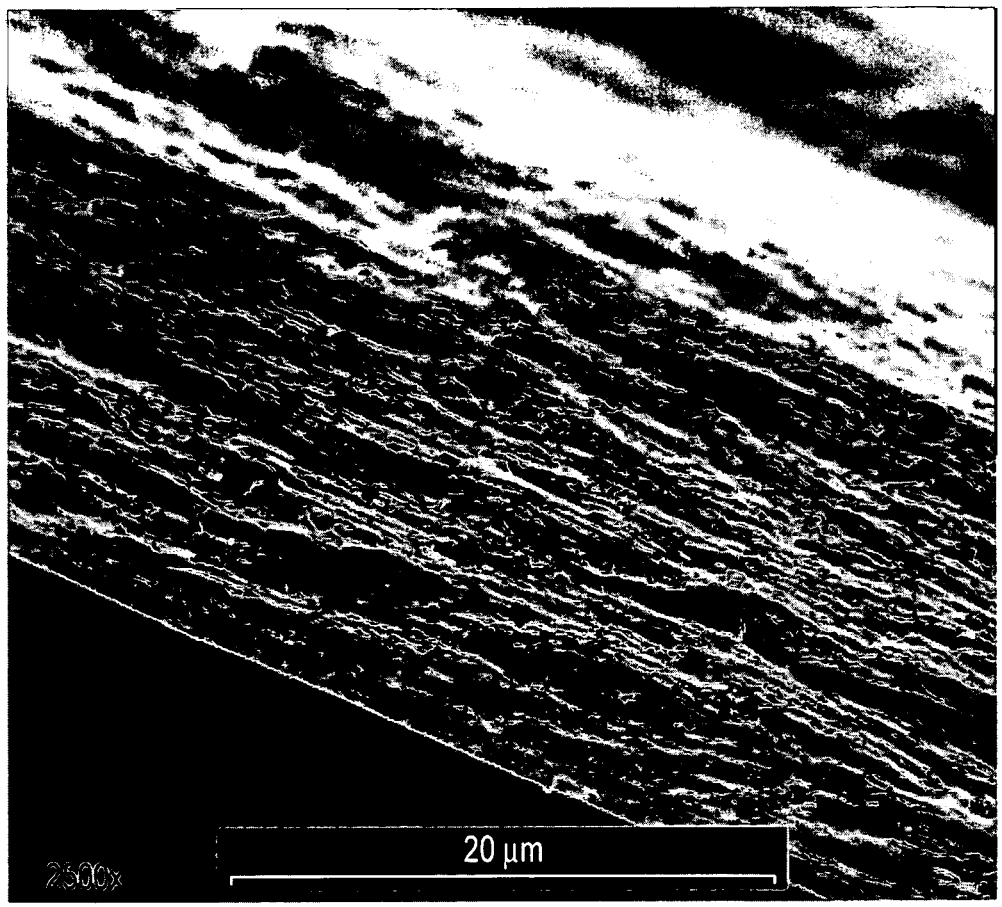

Prior to using the collagen foil to repair visceral membrane tissue of a mammal, the dry collagen foil material may be hydrated. FIG. 10 is a SEM photograph illustrating the surface of a hydrated collagen foil wherein collagen fibrils are clearly shown. Substantial non-porosity of the surface is evident from the picture.

Figure 12A:
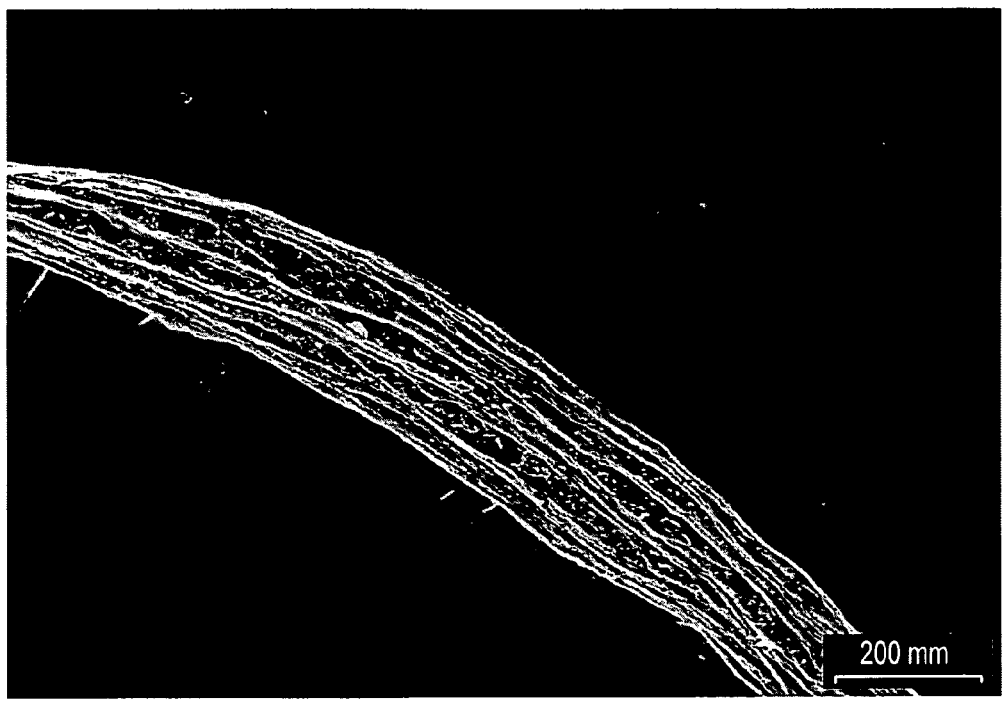
FIGS. 12A and 12B are SEM photographs illustrating the cross section of a dry biofunctional collagen foil biomatrix according to embodiments of the present invention.
Figure 12B:
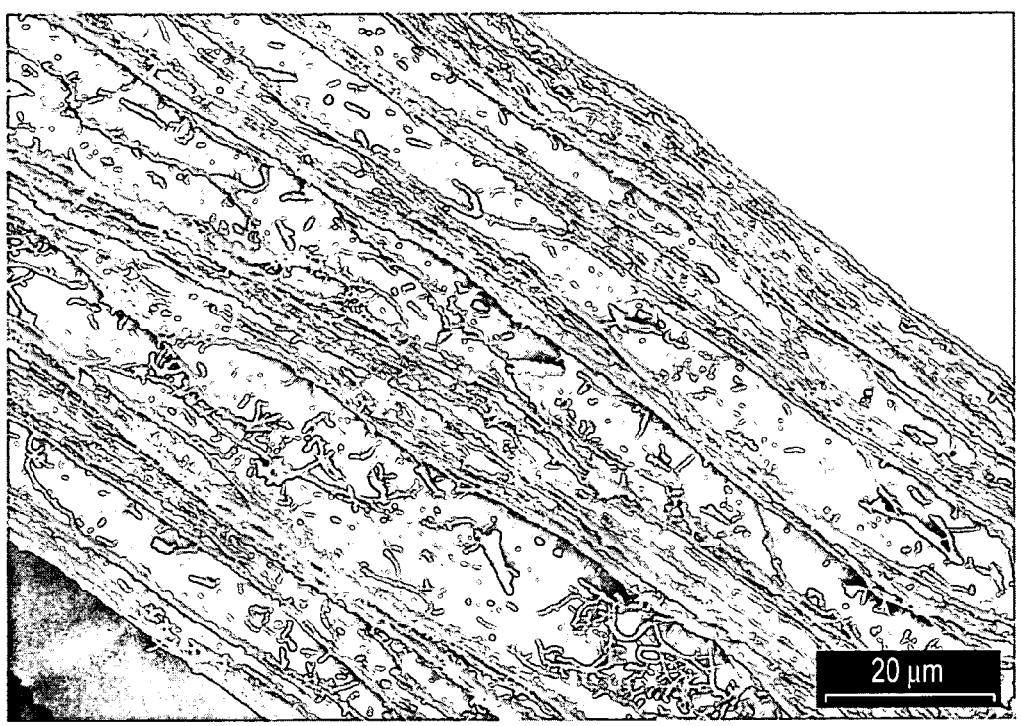

According to some embodiments, the collagen foil biomatrix is substantially nonporous, and interstices exist between the layers of collagen fibrils. The collagen foil biomatrix can be analogous to a stack of pages wherein each page is substantially smooth and nonporous, with a space between each page. When in its dry form the interstices can be more pronounced. The interstices become reduced when the collagen foil biomatrix is observed under near natural conditions in a slightly humid atmosphere. The reduction of the interstices of the collagen foil biomatrix and the layered characteristics are illustrated in pictures of cross sections of collagen foil biomatrix in a humid atmosphere in FIGS. 11A-C. Humid ESEM conditions may approach natural conditions. The material reveals a structure like a stack of sheets packed very tightly together. Interstices between the collagen layers are evident. In comparison, FIGS. 12A-B are ESEM photographs showing a dry collagen foil. Multiple layers of collagen and interstices between the collagen layers are evident. In addition to promoting liquid-tight and air-tight properties, the numerous parallel-oriented thin collagen fibril layers of the collagen foil biomatrix simultaneously serve as a bioequivalent biofunctional scaffold for cell in-growth for de novo construction of the body's own tissue.

In some cases, the change in volume of the collagen foil biomatrix is small or negligible when hydrated. The collagen foil biomatrix substantially retains its size and shape upon being hydrated, having excellent shape stability even after hydration, and causing no problems of swelling or shrinking following the contact with the tissue. Once hydrated and implanted, collagen foil biomatrix embodiments may not significantly expand or contract in area or thickness to the extent that it would tear surgical sutures or break apart fibrin or other biocompatible glue seals that hold the collagen foil biomatrix to the patient's tissue.

In some cases, the shrinking or swelling of the area of the dry collagen foil biomatrix may vary from about −5% to about 20% when completely hydrated. In some case, the area of the dry collagen foil biomatrix may vary between about −5% to about 10% when completely hydrated. Optionally, the area of the dry collagen foil biomatrix can vary between about −5% to about 5% when completely hydrated. For example, the area of the dry collagen foil biomatrix may increase no more than about 4 percent when completely hydrated.

In some cases, the collagen foil biomatrix increases up to about 6 times its dry thickness when it is completely hydrated. In some cases, the collagen foil biomatrix increases up to about 3 times its dry thickness when it is completely hydrated. In some cases, the collagen foil biomatrix increases to about twice its dry thickness when it is completely hydrated.

The thickness of the collagen foil biomatrix may vary depending on the particular application. Varying the amount of starting material utilized to produce a particular size of collagen foil biomatrix can control the thickness of the collagen foil biomatrix. In some cases, the collagen foil biomatrix, when in its dry form, has a thickness between about 0.01 mm to about 3.0 mm. In another example, the collagen foil biomatrix has a thickness between about 0.02 mm to about 2.0 mm. In a further example, the collagen foil biomatrix has a thickness between about 0.03 mm to about 1.5 mm. In another example, the collagen foil biomatrix has a thickness between about 0.05 mm to about 1 mm. In still another example, the collagen foil biomatrix has a thickness of about 1.0 mm or less.

The dry weight of the collagen foil biomatrix may be dependent on its desired thickness. In one example, the dry weight of the collagen foil biomatrix is between about 1 mg/cm$^2$ to about 50 mg/cm$^2$. In another example, the dry weight of the collagen foil biomatrix is between about 1.5 mg/cm$^2$ to about 30 mg/cm$^2$. In still another example, the dry weight of the collagen foil biomatrix is between about 2 mg/cm$^2$ to about 20 mg/cm$^2$. In a further example, the dry weight of the collagen foil biomatrix is between about 2.5 mg/cm$^2$ to about 15 mg/cm$^2$. For example, the dry weight of the collagen foil biomatrix can be between about 3 mg/cm$^2$ to about 10 mg/cm$^2$.

In some cases, the weight of the collagen foil biomatrix increases up to about 15 times its dry weight upon hydration. In another example, the weight of the collagen foil biomatrix increases up to about 10 times its dry weight upon hydration. In another example, the weight of the collagen foil biomatrix increases up to about 7 times its dry weight upon hydration. In still another example, the weight of the collagen foil biomatrix increases up to about 5 times upon hydration from its dry state.

According to some embodiments, the collagen foil biomatrix beneficially has high tensile strength, which improves and supports the handling of the collagen foil biomatrix, for example during its surgical application, and provides an increased mechanical stability, for example after its implantation. Additionally, increasing the thickness of the collagen foil biomatrix can significantly increase the tensile strength.

The propensity of collagen foil biomatrix material to tear under exerted pressure may be measured as its "ultimate tensile load" or "ultimate tensile force," hereinafter referred to as "ultimate tensile force." The ultimate tensile force of a collagen foil biomatrix may be determined by subjecting pressure to a strip of collagen foil biomatrix having a specified width and determining the amount of pressure applied that results in failure (e.g., tearing or rupturing) of the collagen foil biomatrix. Ultimate tensile force may be quantified using the following equation: "Ultimate Tensile Force"=force applied/width of collagen foil biomatrix strip=Newtons/cm-strip.

In some cases, the collagen foil biomatrix has an ultimate tensile force between about 1 and about 30 Newtons/cm-strip. In some cases, the collagen foil biomatrix has an ultimate tensile force between about 1.5 and about 15 Newtons/cm-strip. In some cases, the collagen foil biomatrix has an ultimate tensile force between about 2 and about 10 Newtons/cm-strip. In some cases, the collagen foil biomatrix has an ultimate tensile force between about 3 and about 6 Newtons/cm-strip. In some cases, a collagen foil biomatrix with an integrated surgical mesh, for example of the type illustrated in FIG. 6B, can have an ultimate tensile force of more than 30 Newtons/cm-strip.

Collagen foil biomatrix embodiments can have a high tensile strength, yet remains elastic and flexible when hydrated. This feature permits a collagen foil biomatrix to optimally adapt to the anatomic conditions (e.g. curves) present at the contact site.

When in its hydrated state, the collagen foil biomatrix can be easily moved around. For example, the biomatrix can be moved around in the surgical site and optimally modeled and adapted to the shape and position of the visceral or parietal membrane defect, e.g. where it is being implanted. Once implanted, the collagen foil biomatrix graft remains smooth and may be repositioned if necessary or desired. Over time, cells and vasculature migrate directed throughout the multiple layers of the multilayered collagen foil biomatrix, eventually replacing the multilayered collagen foil biomatrix with a new tissue and autologous collagen structures. As cells migrate and vasculature forms within the layers of the collagen foil biomatrix, the tissue takes on the form of the collagen foil biomatrix in a directed way. After cellular organization of the collagen foil biomatrix with the newly formed connective tissue, adhesion formation to adjacent tissues, e.g. to the parietal pleura or chest wall, can be minimized.

Collagen for use in manufacturing the collagen foil biomatrix may be obtained from any suitable source. For example, without limitation, collagen may be of bovine, ovine, porcine, equine, or human origin. The collagen may be harvested from a naturally occurring tissue, such as tendon, corium, or other collagen rich tissue or may be produced by recombinant genetic means. As described below, one exemplary embodiment of the invention utilizes equine collagen derived from Achilles tendon.

According to some embodiments, a collagen biomatrix includes native equine collagen fibrils (mainly type I collagen) precipitated from purified minced equine Achilles tendon. A flexible formstable and elastic biomatrix can have a nonporous fluid-tight and air-tight multilayer structure. In a dry state, the biomatrix thickness may be about 0.1 mm, and in a wet state the membrane thickness can be about 0.3 mm.

A multilayered collagen foil biomatrix according to embodiments of the present invention can include a collagenous native cross-linked microscopically multilayered biomatrix having multiple layers of a substantially nonporous foil that includes collagen fibrils. Embodiments of such non-naturally occurring biomatrices are described in the international patent application WO 04/108179 and WO 07/137839, the disclosures of which are incorporated herein by reference in their entirety. Collagen foils which may be used according to embodiments of the present invention are typically biofunctional, bioactive, mechanically stable, elastic, nonporous, air-tight and fluid-tight, especially blood and cell tight, and can provide a temporary barrier against uncontrolled distribution of blood, fibrinogen, necrotic material and damaged tissues. A defined bioactive separation layer between the visceral tissue and the adjacent anatomical structures thus initially shields the treated tissue. A multilayered collagen foil biomatrix can act as a hemostatic agent and inhibit uncontrolled fibrin band formation and distribution as well as hematomas, which are one of the main causes for fibrosis and adhesion formation, in anatomical areas which are located beside or close to visceral membranes, e.g. the lung surface.

A mechanically stable, elastic, nonporous, and primary fluid-tight and gas-tight collagenous biomatrix can be applied to a visceral membrane defect. The collagen biomatrix can acts as an artificial epithelium/mesothelium and cover and protect the visceral or parietal surface. This results in the primary closure of the seal of fluid and air leaks at the organ surface. Advantageously, application of the collagen biomatrix can provide an immediate mechanical sealant, acting as a barrier for fluid or air. Due to the layered structure of the biomatrix, fibroblasts or wound healing cells such as lymphocytes or macrophages can be directed or allowed to migrate throughout the biomatrix, leading to the production of endogenous collagen. Accordingly, the patient's own visceral or parietal membrane can be regenerated or enhanced, for example as the wound healing cells are eventually replaced with normal visceral membrane. In this way, the biomatrix can be remodeled into the body's own visceral membrane. This can be accomplished with little or no adhesions or binding, particularly between the visceral tissue and adjacent areas, e.g. the lung surface and the chest wall.

According to some embodiments, visceral membrane regeneration with a collagen biomatrix can replace or augment certain standard surgical techniques. For example, pleura regeneration can be carried out instead of lung sealing, coagulation techniques, suture techniques, and implantation of other "biomaterials". Biofunctional collagenous biomatrices can be used for the steering of cell ingrowths and enhanced de novo formation of extracellular matrix for the regenerative processes of visceral membranes. A collagen biomatrix can adheres to the wound surface, initially through adhesive forces. The native collagen fibrils of the biomatrix can activate coagulation and the local formation of fibrin, which additionally supports the closure of leaks, and the adherence of the collagen membrane. Bioactive collagen can attract repair cells, especially fibroblasts. This may additionally be supported by the local presence of fibrin (e.g. physiologic fibrin sealant).

Parallel layers in a structured multilayer biomatrix can direct the ingrowth of fibroblasts and repair cells, along the layers. The ingrowths along the parallel layers of the collagen matrix are typically faster than through the layers. The de novo formation of the extracellular matrix with endogenous collagen is also guided through the cell (fibroblast) line up. This process steers the remodeling of the biomatrix to living tissue, and closes the visceral defect, for example after traumatic rupture, surgical incisions, resection or decortication. In a decortication process, the surface layer membrane of the lung is removed.

In this way, embodiments of the present invention encompass techniques for forming a multilayered extracellular matrix resulting from collagen structure of the collagen foil. A steering collagen biomatrix provides for directed cell ingrowth for the regeneration of visceral and parietal membranes. Such steered regeneration of tissue is well suited for closing or reducing leaks in pleural tissue, such as prolonged post-surgical pulmonary air leaks. In fact, animal studies have demonstrated the efficiency of a collagen biomatrix in the prevention of prolonged postoperative air leaks in pulmonary surgery, and in the steered regeneration of visceral membranes through directed cell ingrowth.

According to some embodiments, the collagen biomatrix of the present invention is an impermeable material for the purpose of sealing and the contact between collagen and blood cells determine platelet aggregation. This interaction with the collagen biomatrix induces the release of coagulation factors and formation of fibrin. The collagen biomatrix can be cut according to necessity and adapted to visceral defect. Collagen biomatrix embodiments of the present invention have proved successful in macroscopic aspects of graft incorporation, preventing early and late air leak in post operative subjects, without harmful reactions to adjacent tissue structures (inflammation, adhesion, fibrosis, necrosis) and in histological assessment of the incorporation process and connective tissue organization. Multilayered collagen foil biomatrix embodiments can attract cells such as repair cells and regeneration cells. Biomatrix materials can direct the cell growth on to the surface of the biomatrix, and provide for the in-growth of repair and regeneration cells. Biomatrix materials can be remodeled to natural tissue after the in-growth and can be resorbed.

Standard collagen based compositions are usually perceived as foreign by the host and often encapsulated. Therefore, recellularization and remodeling to the respective anatomical tissue does not occur or is impossible, there is no directed cell in-growth and no control of the regeneration process, and the collagen is merely tolerated as a "biocompatible" implant. In contrast, the multilayered collagen foil biomatrix according to embodiments of the present invention acts as a membrane (e.g., visceral pleura membrane) functioning as a bioactive temporary layer directing cell growth within the multilayered collagen foil biomatrix and on the surface of the collagen foil biomatrix. Rather than acting solely as a barrier against cell growth, as most anti-adhesion compositions do, the multilayered collagen foil biomatrix can be extremely bioactive and support the remodeling of the tissues. For example, within weeks after implantation, a multilayered collagen foil biomatrix can be well integrated into the restored anatomical structure of visceral membrane tissues. Further, during and after surgery, the nonporous, fluid-tight (e.g., blood, liquid, air, gas, bile, etc.) multilayered structure of the collagen membrane is capable of preventing uncontrolled distribution of blood (e.g., fibrinogen/fibrin) and necrotic material from the pleural wound areas, which may be responsible for supporting conditions of adhesion formation in the initial time period after surgery (in contrast to porous compositions). The collagen biomatrix can also prevent direct contact between the visceral surface and the adjacent tissues such as the lung surface and parietal pleura or chest wall, a primary area of the scar formation and fibrosis. This contributes also to the controlled remodeling of anatomical structures with prevention and minimization of uncontrolled adhesion and scar formation and pleural fibrosis. Such techniques can be used in any mammal, including without limitation humans, dogs, cats, mice, rats, and the like.

In addition to promoting liquid-tight and air-tight properties, the numerous parallel-oriented thin collagen fibril layers of the collagen foil simultaneously serve as a biomatrix scaffold for cell ingrowth for de novo construction of the body's own visceral membrane. It has been surprisingly discovered that the nonporous, layered structure of the collagen foil promotes the ingrowth of cells, vasculature, and the formation of new collagen structures across the collagen foil and in the interstices that exist between its multiple layers, forming a neo-pleura with a typical layer structure of a natural pleura within weeks of implantation. As described elsewhere herein, the ingrowth of cells, vasculature, and new collagen structure is so extensive that within weeks post-operation, the neo-pleura becomes difficult to distinguish from a patient's previously existing visceral pleura tissue. Hence, eventually the graft ingrowth may become fully organized.

According to some embodiments of the present invention, a significant benefit of using the collagen foil is the substantially low risk of transmitting a disease to a patient in which it is implanted. Manufacturing process in which the collagen fibrils are treated with acids (e.g., hydrochloric acid, acetic acid, and the like) and bases, such as sodium hydroxide, to produce the collagen foil beneficially acts to inactivate or reduce the infectious levels of bacteria, viruses, and prions that may be present. Treatment of biomaterial with hydrochloric acid, sodium hydroxide, ethylene oxide (ETO), and the like have been recognized by governmental agencies as approved methods within drug and biomaterial regulations to inactivate prions and viruses. Such treatment may, under some regulations, reduce the regulatory requirements for testing the collagen foil on a batch-by-batch basis. Thus, the treatment of the collagen fibrils during the manufacturing process enhances the product safety and reduces the risk of disease transmission to a patient.

Collagen material that has been subjected to the manufacturing process described herein is not known to transmit any pathogens to patients. Thus, in addition to the manufacturing process, utilization of equine collagen further avoids the risks of transmitting spongiform encephalitis that have been previously associated with human cadaveric substitutes. Use of collagen derived from an equine origin, such as collagen derived from equine Achilles tendons avoids the risks of transmitting transmissible spongiform encephalopathy (TSE), which is also known as bovine spongiform encephalopathy (BSE) or scrapie. Transmission of this disease has been associated with the use of biological material obtained from ruminant sources (e.g., biological material from cattle, goats, sheep, and the like).

The change in volume of the collagen foil is small or negligible when hydrated. In contrast to porous replacement products, the collagen foil substantially retains its size and shape upon being hydrated, having excellent shape stability, remaining biostable even after hydration, and causing no problems of swelling or shrinking in the body following implantation. Once hydrated and implanted, collagen foil does not significantly expand or contract in area or thickness to the extent that it would tear surgical sutures or break apart fibrin glue seals that hold the collagen foil to the patient's tissue.

The thickness of the collagen foil can be controlled by varying the amount of starting material utilized to produce a particular size of collagen foil. The collagen foil can be gas-sterilized with ethylene oxide (ETO) or similar sterilization gas or by irradiation.

Manufacture of Collagen Biomatrix

According to some embodiments, the collagen foil is a biomatrix of collagen fibrils treated to remove cellular components and to form a sheet of collagen fibrils. During the manufacturing process, for example as described in WO 04/108179 or WO 07/137839, the collagen fibrils become naturally cross-linked as the fibrils precipitate out of solution to form a collagen foil. Unlike cross-linking the collagen fibrils with chemicals or radiation (e.g. ionizing or ultraviolet radiation), allowing natural cross-linking of the collagen fibrils can ensure their biofunctionality, promote accelerated regeneration, and reduce resorption times once the collagen foil biomatrix is brought into contact with the tissue. Cross-linking collagen fibrils with chemicals or radiation can result in increased resorption times, or even non-resorption, encapsulation, and scar formation. The natural cross-linking of the fibrils in the collagen foil biomatrix utilized in some embodiments occurs by natural, physiological-like means. Primarily this natural cross-linking is through non-covalent interactions (e.g. van der Waals or dipole-dipole interactions) or by the formation of readily dissociable Schiff-base bonds between the amino acid side chains of the collagen molecule. Intermolecular cross-linking of collagen is responsible for physical and chemical stability. A key step in the formation of collagen cross-links depends on the enzymatic conversion of lysine or hydroxylysine residues and gives rise to aldehydes, allysine and hydroxyallysine. These aldehyde groups spontaneously react with reactive amino groups resulting in the formation of Schiff-base components containing labile aldol-condensation products with labile aldimine links (like for example —CH=N—). Thus, the fibrils of the product may be dissociated by treatment with, for example, a weak acid. Cross-linking arising from the use of chemical cross-linking agents can be detected from the presence of stable covalently cross-linked cross-linking moieties. Commonly, this is accomplished by using a Schiff-base reagent (e.g. glutaraldehyde) to form Schiff-base reaction products, and then stabilizing the bonds through either an Amadori-rearrangement or reducing conditions. In addition collagen can be cross-linked by various bifunctional carbodiimide reagents. Cross-linking arising from the use of radiation can be detected by the presence of stable covalent bonds between the collagen fibrils, caused by the reaction of free radical moieties generated during irradiation. The fibrils in the biomatrix product, on the other hand, are substantially uncross-linked with any stable covalent bonds, and have not been treated in a chemical or irradiative manner. Thus, any associations between the fibrils in the biomatrix product are substantially non-covalent or readily reversible, and are not stably cross-linked. Chemicals such as cyanamide, glutaraldehyde, formaldehyde, acrylamide, carbodiimidediones, diimidates, bisacrylamides, and the like have been utilized in the past to chemically cross-link collagen fibrils. Use of such chemicals, however, may result in toxicity risks associated with inadvertently contacting visceral tissue with residual chemicals in the collagen foil biomatrix. The precipitation process thereby avoids the toxicity risks of cross-linking chemicals and longer resorption times associated with cross-linking the collagen fibrils with chemicals or radiation.

In some cases, the resulting dried, precipitated, collagen composition forms a collagen foil biomatrix having a high-molecular weight multi-layered collagen membrane that includes numerous layers of two-dimensionally multi-directional naturally intertwined collagen fibrils. The collagen foil biomatrix may primarily contain interstitial Type I collagen. The collagen foil biomatrix may have substantially no pores and can be primarily liquid-tight and air-tight. Immune diffusion tests may be conducted on the product to guarantee the absence of foreign protein. The collagen foil biomatrix may be gas-sterilized with ethylene oxide (ETO) or similar sterilization gas or by irradiation.

A significant benefit of using an collagen foil biomatrix is the substantially low risk of transmitting a disease to a patient being contacted with said foil. The manufacturing process in which the collagen fibrils are treated with acids (e.g. hydrochloric acid, acetic acid, and the like) and bases, such as sodium hydroxide, to produce the collagen foil beneficially acts to inactivate or reduce the infectious levels of bacteria, viruses, and prions that may be present. Treatment of biomaterial with hydrochloric acid, sodium hydroxide, ethylene oxide (ETO), and the like have been recognized as approved methods within drug and biomaterial regulations to inactivate prions and viruses. Such treatment may, under some regulations, reduce the regulatory requirements for testing the collagen foil on a batch-by-batch basis. Thus, the treatment of the collagen fibrils during the manufacturing process enhances the product safety and reduces the risk of disease transmission to a patient.

Additionally, embodiments encompass the use of a multi-layered collagen foil biomatrix in the manufacture of a medicament, i.e. a medically applicable material, for treating a disorder such as e.g. injuries, surgeries, or pathogen-based diseases, in a mammal characterized by a defect in the visceral membrane or surrounding tissue.

According to some embodiments, a collagen foil can be produced from suspensions of high molecular weight collagen fibrils through a controlled drying process. A graded precipitation of the collagen fibril suspension results from the evaporation of water and simultaneous pH elevation. The controlled drying process results in a multi-layered construction of a collagen foil that can be implanted by surgeons. The multi-layered collagen foil construction provides a number of properties that are beneficial in a pleural substitute and as a biomatrix for the regeneration of living pleural tissue.

In one embodiment, the process to produce the collagen foil removes all cellular components producing a collagen foil of collagen fibrils that primarily includes acellular components.

Using established procedures in collagen chemistry, collagen-containing tissue can be used as a starting material for the preparation of the collagen foil. In one embodiment, tendons, such as Achilles tendons, are used as a starting material. In a further embodiment, equine Achilles tendons are used as a starting material. According to some embodiments, collagen can be obtained from any of a variety of animals, including without limitation sheep, monkeys, cows, horses, rats, mice, humans, or laboratory animals. Hence, collagen can be derived from a bovine source, a porcine source, an equine source, an ovine source, a primate source, a rodentia source, or a human source, for example.

In one embodiment, the starting material, for example equine Achilles tendons, is first ground and treated for at least one hour with 1 N sodium hydroxide and neutralized with hydrochloric acid. The collagen starting material is treated in acid conditions at pH 2. The acid utilized may be hydrochloric acid, acetic acid, or the like. Subsequently, the non-collagenous proteins and intermolecular cross-linking bonds present in the starting material are degraded enzymatically with pepsin to form a suspension of collagen. The suspension is then neutralized. In one embodiment, the suspension is neutralized to between about pH 6.5 to about pH 8.0. In another embodiment, the suspension is neutralized to between about pH 6.9 to about pH 7.5. In another embodiment, the suspension is neutralized to about pH 7. The collagen suspension is centrifuged, the supernatant removed, and the precipitate resuspended in acetic acid at about pH 2-4.5. Non-collagenous proteins are thereby successfully removed from the suspension of collagen. Repetition of the above-described steps may be conducted as necessary to remove residual non-collagenous proteins present in the precipitate.

A surprising result of the production process of the equine collagen foil is that a controlled pH elevation of the collagen suspension in acetic acid is achieved due to the specified removal of water by evaporation over a long period of time, e.g., 24 hours. The specified elevation of pH causes the precipitation of the multi-directional intertwined collagen fibrils in two-dimensional direction layers forming a multi-layered construction of the equine collagen foil. In one embodiment, the process is performed in a drying oven at a temperature of about 20° C. to about 55° C., with equipment to remove steam and the simultaneous steam neutralization of acetic acid. In another embodiment, the process is performed in a drying oven at a temperature of about 30° C. to about 45° C.

The equine collagen foil that results from the production process can be considered to be in its dry form when further loss of water is not detected or is negligible. The water content of the "dry form" of equine collagen foil is typically between about 2% to about 18% by weight. The relatively high residual water content present in the "dry form" of the equine collagen foil prevents or restrains the denaturation of collagen molecules that comprise the equine collagen foil.

The above-described process is responsible for the precipitation of the collagen fibrils from the suspension since components with low solubility fall out at the beginning of the process at a low pH elevation. This technique results in a precipitation of collagen fibrils during water evaporation and simultaneous pH elevation.

Processes utilized to produce a collagen foil biomatrix can form stacked layers of collagen fibrils. Between each layer of collagen fibrils are interstices into which cells and vasculature of the patient can migrate and form new collagen structures and native-conformation tissue. It is a beneficial property of some embodiments that the biofunctional native collagen fibers and the nonporous, layered structure of the collagen foil biomatrix promotes the in-growth of cells, vasculature, and the formation of new collagen structures across the collagen foil biomatrix and in the interstices that exist between its multiple layers. As compared to random, unguided, non-controlled cellular in-growth at the wound or defect, the directed in-growth and regeneration according to method embodiments can inhibit or prevent the formation of adhesions and fibrosis. Thus, pain and complications associated with adhesions and fibrosis can be avoided.

According to some embodiments, the purification process for producing the equine collagen foil begins with at least one hour of sodium hydroxide solution treatment of the tendon starting material, followed by neutralization in hydrochloric acid. Pepsin is then used to break down the tendons. The colloidal collagen thus produced is precipitated as fibrils. Drying and gas sterilization then yields equine collagen foil with 5.6 mg of native collagen fibrils per square centimeter. Nothing else is added and no artificial methods for cross linkage (i.e. involving chemicals or radiation) are performed. Immunodiffusion tests ensure that no foreign proteins are present. An equine collagen foil can be made of native equine collagen fibrils (mainly interstitial type I collagen). One square centimeter of the material can contain 5.6 milligrams of collagen fibrils with no cellular components. Fibrin glue, such as Tissucol™ Duo S (Baxter), can be used to attach the grafts to the visceral membrane or outer wound surface. This biological dual-component glue kit includes of a pre-filled syringe containing human plasma proteins, fibrinogen, clotting factor XIII, plasma fibronectin and aprotinin, and another pre-filled syringe containing thrombin and calcium chloride.

Experimental Animals

The following example presents the results of experiments in pigs to evaluate a collagen foil for its suitability as a visceral pleura substitute used to repair visceral pleura defects and as a biomatrix for visceral pleura regeneration. For the experiments, 5 Landrace pigs, around 35 kg of weight, pigs were used. The animal studies were performed after formal approval by the authorities of the Ethic Committee of the Catholic University of Italy. The choice of this species and this weight is due to the similarity of the swine pulmonary parenchyma with the human one. The dimensions of the animals allow us to use the surgical instrumentation normally used in humans and act as an ideal animal model for human subjects. Before surgery, the animals were prepared at the "Laboratory animal facility of Holy Heart University (Rome)" for a period of 5 days. The day of the intervention the animal was set in general anaesthesia through the following procedure:

Anaesthesia:

Preanaesthesia through an intramuscular injection of: Atropin 0.02 mg/kg+Ketamine 15 mg/kg+Diazepan 0.1 mg/kg; induction with mask for anaesthesia with $O_2$ and vapours of Isoflurane 2%; endotracheal intubation and maintenance with $O_2$ and vapours of Isofluorane 1.5%; muscular relaxing with pancuronium bromide (0.1 mg/kg e.v.).

Figure 13:
FIG. 13 shows lung tissue with tissue defects or leaks and air leaks after the resection of the pleural visceral membrane.
Figure 14:
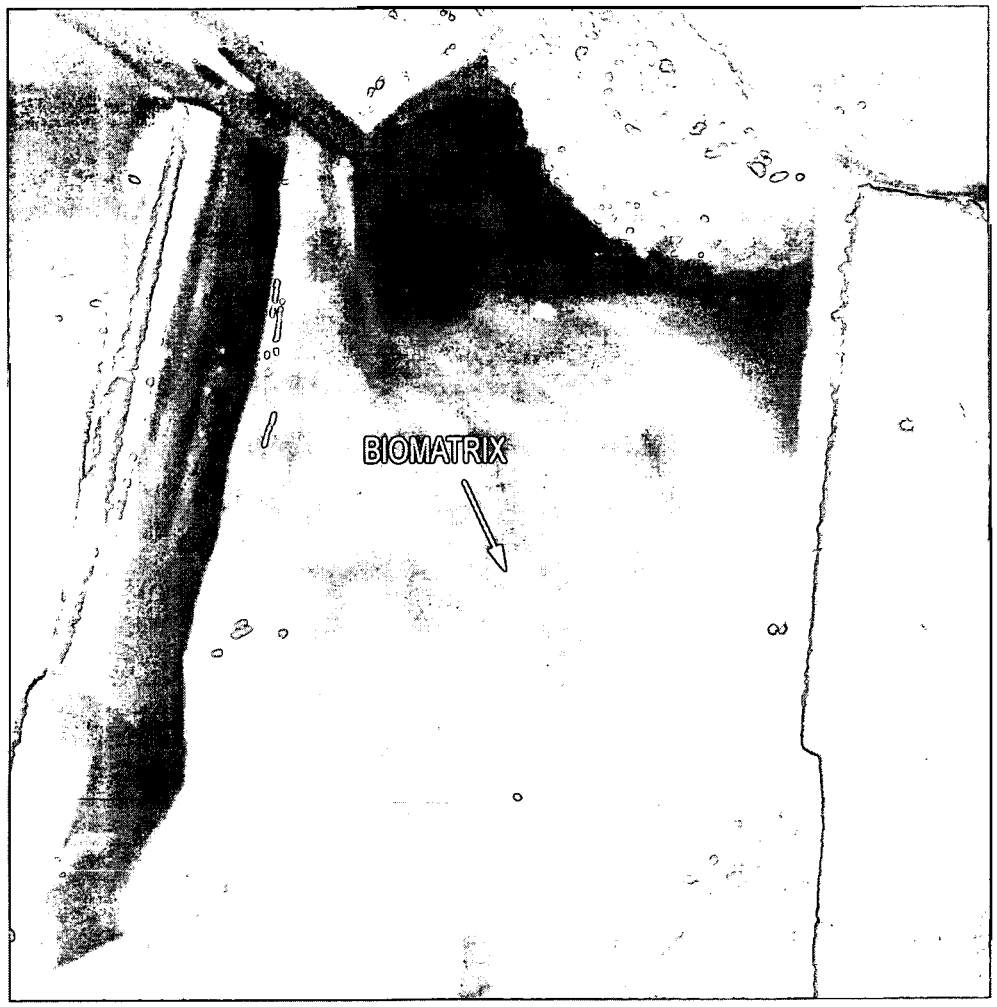
FIG. 14 shows application of the collagen foil on the wound surface, according to embodiments of the present invention.

Surgical Procedure:

After the induction of anaesthesia, the animals were maintained in lateral decubitus and a lateral thoracotomy on the fourth intercostal space was performed. Visceral pleura was damaged to obtain bleeding and air leak, as indicated in FIG. 13. A piece of the collagen biomatrix (measuring 3.5×2.5 cm) was then cut to size and immersed for 5 minutes in sterile 0.9% saline, and applied to the damaged visceral pleura, as depicted in FIG. 14. To close the defect, the graft was tucked all round under the pleural whole margins and sealed with fibrin sealant to keep it in place, and to assure a water-tight or fluid-tight closure. The collagen biomatrix includes native equine collagen fibrils (5.6 mg/cm$^2$) purified from minced equine Achilles tendon, and the fibrin sealant includes Tissucol™ Duo S (Baxter).

Figure 15:
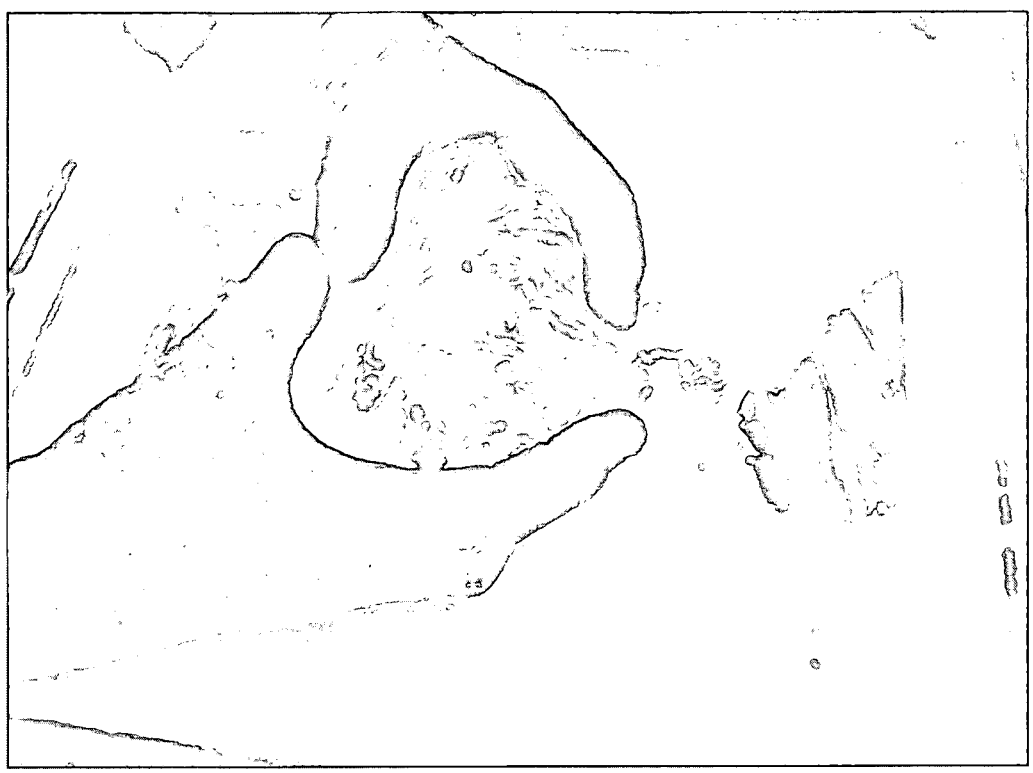
FIG. 15 shows post application tissue leak or air leak evaluation under water (hydro pneumatic test) of the lung, according to embodiments of the present invention.
Figure 16:
FIG. 16 shows a collagen foil covering the lung tissue and providing a liquid-tight and air-tight closure while protecting the cellularity of the tissue, according to embodiments of the present invention.

To detect any post application air leak, the aerostatic power of the collagen biomatrix was evaluated through a hydro pneumatic test, as shown in FIG. 15. The lung was covered with saline solution and the lung insufflated by the anaesthesiologist. In absence of an air leak, a water-drainage was removed before the animals were revived. In case of air leak, water-drainage was connected with a system of measurement of the air leak. As depicted in FIG. 16, the collagen foil covers the lung tissue and provides a water-tight or air-tight closure while protecting the cellularity of the tissue.

The thoracotomy was sutured in layers with absorbable thread and the skin sutured in silk. The animals were revived and observed at the laboratory animal facility for 7, 15, 21 and 28 days during which the entity of the possible air leak was appraised.

Post-operative analgesic (Ketoprophene, Findol 10%, 0.3 ml/10 kg/die, intramuscularly) and antibiotic (enrofloxacin 2.5 mg/kg/die i. m.) therapy was lengthened for 7 days. The animals were given conventional mixed feed because the drainage did not interfere with physiological functions. Every day the health of the animal was monitored. At the VIII, XVI, XXII and XXIX day, the animals have been again submitted to general anaesthesia through bronchial intubation, and rethoracotomy again performed to the fifth intercostal space through cutaneous incision along the intercostal space. After incising the intercostal muscle, a costal retractor (Finocchietto) and an autostatic abdominal retractor were placed in site. After the opening of the pleural space, the lobe, or the whole lung, previously treated with collagen biomatrix, were removed. The thoracotomy was sutured with Vicryl 2 and the skin with silk 1. At the end of the procedures, the animal, still in general aesthesia, were euthanized with Tanax E.V. (3 ml/10 kg).

Results:

Anaesthesia, surgery and the postoperative follow-up periods were uneventful in all but two animals. None of the animals displayed signs of inflammation, or impaired wound healing. No persistent air leakage was observed either short term or long after surgery as is demonstrated in the data. The biomatrix was remodeled into a pleura-like visceral membrane, smooth and plane without signs of clinically relevant adhesions or fibrosis.

Histological Slides: Week 2

Figure 17:
FIG. 17 shows a histological slide of lung tissue defects sealed with a collagen foil biomatrix fixed with fibrin sealant, according to embodiments of the present invention.
Figure 18:
FIG. 18 shows a histological slide of lung tissue sealed with fibrin sealant which shows high affinity of cells, according to embodiments of the present invention.
Figure 19:
FIG. 19 shows a histological slide of a collagen biomatrix (lower part of slide) sealing tissue defects according to embodiments of the present invention.
Figure 20:
FIG. 20 shows fibroblasts recruited and growing within the interstices of the collagen biomatrix according to embodiments of the present invention.

FIG. 17 shows a histological slide of lung tissue sealed with collagen foil biomatrix in conjunction with fibrin sealant, according to embodiments of the present invention. FIG. 18 shows a histological slide of lung tissue sealed with fibrin sealant which shows high affinity of cells, according to embodiments of the present invention. FIG. 19 shows a histological slide of a collagen biomatrix (lower part of slide) sealing lung tissue and within the collagen biomatrix, cells are colonizing promoting tissue growth. FIG. 20 provides a close up of FIG. 19, which shows fibroblasts recruited and growing within the interstices of the collagen biomatrix.

Histological Slide: Week 4

Figure 21:
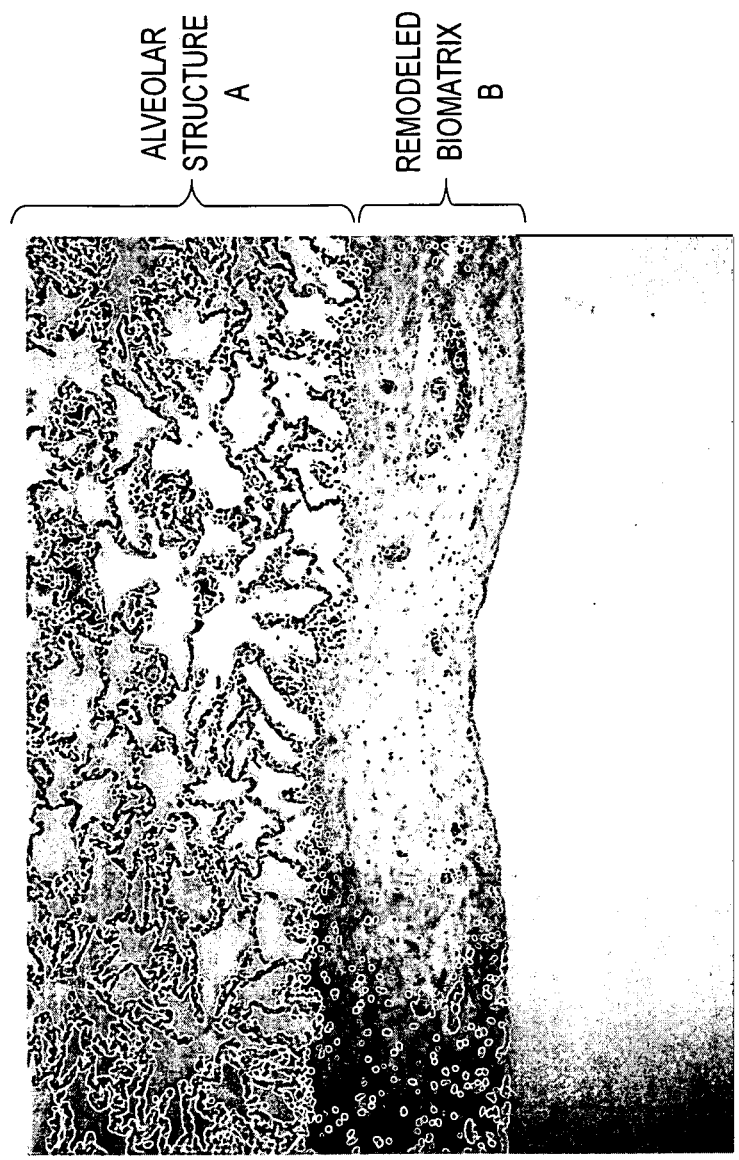
FIG. 21 depicts a normal histological aspect of the pleural visceral membrane on the surface of the lung tissue.

FIG. 21 shows remodeled collagen biomatrix four weeks after implantation. The original lamellar structure of the collagen biomatrix is remodeled into lamellar autologous tissue. Endogenous collagen synthesis generates a neo-pleura, which exhibits the same parallel, lamellar structure as normal visceral pleura. As a result of the parallel structure of the collagen biomatrix, the endogenous synthesized collagen layers show also the parallel, lamellar structure. No inflammatory reaction at the borderline between the remodeled biomatrix/neo-pleura and the lung tissue is evident. Portion A illustrates alveolar structure, and Portion B illustrates remodeled biomatrix/neo-pleura with a lamellar collagen structure including repair cells (mainly fibroblasts) and blood vessels.

Figure 22:
FIG. 22 shows remodeled collagen biomatrix and regenerated visceral membrane four weeks after implantation, according to embodiments of the present invention.

FIG. 22 depicts a normal histological aspect of the visceral pleura on the surface of the lung. Portion A illustrates alveolar structure, and Portion B illustrates pleura visceralis with a lamellar collagen structure including cells fibroblasts and blood vessels.

As shown by these experiments, a biofunctional collagen foil biomatrix can be placed over the edges of a surgically produced defect in the visceral pleura, and on top of the outer lung surface, in order to direct cell in-growth and control tissue regeneration, thus preventing adhesion of the regenerating wound tissue to the parietal pleura and chest wall. The edges of the biofunctional collagen foil biomatrix may be secured to portions of the visceral pleura near the defect. The structure of the biomatrix surface can be nonporous and form a mechanically stable temporary fluid- and air-tight barrier between the outer lung surface and the pleural cavity. Pleural fibroblasts can invade the biomatrix and spread in a directed longitudinal in-growth along the parallel multi-layered structures, growing into the collagen foil biomatrix, as directed by the multi-layer structure. The multilayered collagen foil biomatrix can be fully integrated. Pleural tissue repair cells can infiltrate the multilayer structure of the collagen biomatrix.

All patents, patent publications, patent applications, journal articles, books, technical references, and the like discussed in the instant disclosure are incorporated herein by reference in their entirety for all purposes.

While exemplary embodiments have been described in some detail, by way of example and for clarity of understanding, the skilled artisan will recognize that a variety of modification, adaptations, and changes may be employed. Hence, the scope of the present invention should be limited solely by the claims.

What is claimed is:

1. A method for treating a disorder in a patient characterized by a defect of a visceral or parietal membrane, comprising the step of administering to the defect a biofunctional nonporous multilayered collagen foil biomatrix which directs visceral or parietal cell growth within interstices of the multilayered collagen foil biomatrix, wherein a material comprising a polyethylene glycol that is separate from the biomatrix is applied to the multilayered collagen foil biomatrix on a first surface of the multilayered collagen foil biomatrix that is to face away from the defect to which the biomatrix is administered and not on a second surface of the multilayered collagen foil biomatrix that faces the defect.

2. The method according to claim 1, wherein the multilayered collagen foil biomatrix forms a substantially liquid tight and air tight layer between the visceral or parietal defect and an adjacent tissue.

3. The method according to claim 1, wherein the administering step comprises one or more methods selected from the group consisting of:
   attaching the multilayered collagen foil biomatrix to the visceral or parietal defect with fibrin sealant, attaching the multilayered collagen foil biomatrix to the visceral or parietal defect with surgical sealant, attaching the multilayered collagen foil biomatrix to the visceral or parietal defect with surgical sutures, utilizing pressure fitting techniques, and utilizing natural adhesion between the multilayered collagen foil biomatrix and the visceral or parietal defect.

4. The method according to claim 3, wherein the multilayered collagen foil biomatrix is attached to the visceral or parietal defect of the patient using a fibrin sealant.

5. The method according to claim 1, wherein the biomatrix does not promote adhesions with an adjacent tissue after cell growth within interstices of the multilayered collagen foil biomatrix.

6. The method according to claim 1, wherein the multilayered collagen foil biomatrix directs cell growth on the outer surface of the multilayered collagen foil biomatrix.

7. The method according to claim 1, wherein the multilayered collagen foil biomatrix comprises an excipient selected from the group consisting of an antibiotic, a preservative, and a growth factor.

8. The method according to claim 1, wherein the multilayered collagen foil biomatrix comprises collagen derived from a source selected from the group consisting of a bovine source, a porcine source, an equine source, an ovine source, a primate source, a rodentia source, and a human source.

9. The method according to claim 1, wherein the multilayered collagen foil biomatrix comprises collagen derived from tendon tissue.

10. The method according to claim 1, wherein the defect comprises a defect of a pleural membrane, and wherein the biofunctional nonporous multilayered collagen foil biomatrix directs pleural cell growth within interstices of the multilayered collagen foil biomatrix.

11. The method according to claim 1, wherein the material comprising polyethylene glycol is applied to the multilayered collagen foil biomatrix prior to administering the multilayered collagen foil biomatrix to the defect.

12. The method according to claim 1, wherein the material comprising polyethylene glycol is applied to the multilayered collagen foil biomatrix subsequent to administering the multilayered collagen foil biomatrix to the defect.

13. The method according to claim 12, wherein the material comprising polyethylene glycol is also applied to tissue adjacent to the defect to which the multilayered collagen foil biomatrix is administered.

14. A method for regenerating a visceral or parietal membrane in a mammal, comprising contacting a defect in the visceral or parietal membrane with a collagen foil comprising a non-naturally occurring biomatrix of multiple layers of collagen fibrils that are not cross-linked by chemicals or radiation, wherein the biomatrix is substantially nonporous, wherein the biomatrix directs visceral or parietal cell growth within interstices of the multilayered collagen foil biomatrix, and wherein a material comprising polyethylene glycol that is separate from the biomatrix is applied to the multilayered collagen foil biomatrix on a first surface of the multilayered collagen foil biomatrix that is to face away from the defect to which the biomatrix is administered and not on a second surface of the multilayered collagen foil biomatrix that faces the defect.

15. The method according to claim 14, wherein the multilayered collagen foil biomatrix forms a substantially liquid tight and air tight layer between the visceral or parietal membrane and an adjacent tissue.

16. The method according to claim 14, wherein the multilayered collagen foil biomatrix is attached to the visceral or parietal defect of the patient using a fibrin sealant.

17. The method according to claim 14, wherein the biomatrix does not promote adhesions with an adjacent tissue after cell growth within interstices of the multilayered collagen foil biomatrix.

18. The method according to claim 14, wherein the defect comprises a defect of a pleural membrane, and wherein the biofunctional nonporous multilayered collagen foil biomatrix directs pleural cell growth within interstices of the multilayered collagen foil biomatrix.

19. A method for directed cell in-growth and controlled tissue regeneration of a visceral or parietal membrane to prevent post-surgical or post-traumatic adhesion and fibrosis formation on the surface of a tissue in a mammal, comprising contacting the tissue with a nonporous microscopically multilayered collagen foil biomatrix, wherein the biomatrix directs visceral or parietal cell growth within interstices of the multilayered collagen foil biomatrix, and wherein a material comprising polyethylene glycol that is separate from the biomatrix is applied to the multilayered collagen foil biomatrix on a first surface of the multilayered collagen foil biomatrix that is to face away from the defect to which the biomatrix is administered and not on a second surface of the multilayered collagen foil biomatrix that faces the defect.

20. The method according to claim 19, wherein the multilayered collagen foil biomatrix forms a substantially liquid tight and air tight layer between a visceral or parietal membrane defect and an adjacent tissue.

21. The method according to claim 19, wherein the multilayered collagen foil biomatrix is attached to the visceral or parietal membrane defect of the patient using a fibrin sealant.

22. The method according to claim 19, wherein the biomatrix does not promote adhesions with an adjacent tissue after cell growth within interstices of the multilayered collagen foil biomatrix.

23. The method according to claim 19, wherein the visceral or parietal membrane comprises a pleural membrane, and wherein the nonporous microscopically multilayered collagen foil biomatrix directs pleural cell growth within interstices of the multilayered collagen foil biomatrix.

* * * * *